(12) United States Patent
Wei et al.

(10) Patent No.: US 8,798,934 B2
(45) Date of Patent: Aug. 5, 2014

(54) REAL TIME MANAGEMENT OF DATA RELATING TO PHYSIOLOGICAL CONTROL OF GLUCOSE LEVELS

(75) Inventors: Charles Wei, Fremont, CA (US); Gary A. Hayter, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 782 days.

(21) Appl. No.: 12/842,838

(22) Filed: Jul. 23, 2010

(65) Prior Publication Data

US 2011/0021898 A1 Jan. 27, 2011

Related U.S. Application Data

(60) Provisional application No. 61/228,101, filed on Jul. 23, 2009.

(51) Int. Cl.
| | | |
|---|---|---|
| *G01N 33/48* | (2006.01) | |
| *G01N 31/00* | (2006.01) | |
| *G06G 7/48* | (2006.01) | |
| *G06G 7/58* | (2006.01) | |
| *A61B 5/145* | (2006.01) | |
| *G06F 19/00* | (2011.01) | |
| *A61M 5/172* | (2006.01) | |
| *A61M 5/142* | (2006.01) | |

(52) U.S. Cl.
CPC ...... *G06F 19/3437* (2013.01); *A61M 2230/201* (2013.01); *A61M 2205/3592* (2013.01); *A61B 5/14532* (2013.01); *G06F 19/345* (2013.01); *A61M 2205/52* (2013.01); *A61M 5/1723* (2013.01); *A61M 2005/14208* (2013.01); *G06F 19/3418* (2013.01)
USPC ............. 702/19; 702/22; 703/11; 703/12

(58) Field of Classification Search
CPC ............ A61M 2230/201; A61M 5/1723;
G06Q 50/22; G06Q 50/24; A61B 5/14532;
A61B 5/7275; A61B 5/4848; G06F 19/3468;
G06F 19/322; G06F 19/3456; G06F 19/3493;
G06F 19/3406; Y10S 128/92
See application file for complete search history.

(56) References Cited

U.S. PATENT DOCUMENTS

| | | | |
|---|---|---|---|
| 2,915,579 | A | 12/1959 | Mendelsohn |
| 3,374,337 | A | 3/1968 | Burley |

(Continued)

FOREIGN PATENT DOCUMENTS

| | | |
|---|---|---|
| AU | 2003/259741 | 2/2004 |
| CA | 2495648 | 2/2004 |

(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner* — Larry D Riggs, II
(74) *Attorney, Agent, or Firm* — Jackson & Co., LLP

(57) ABSTRACT

Continuous glucose monitoring (CGM) data and insulin delivery data are used to generate more reliable projected alarms related to a projected glucose levels. A memory stores endogenous data related to measurements of glucose level in a patient, and also stores exogenous data, such as insulin on board, both of which are used by a processor to create projected alarms. Profiles of CGM data are created for use in tuning patient-specific insulin data, such at basal rate, carb ratio, and insulin sensitivity. A processor searches for patterns in the data profiles and if found, recommended changes to patient-specific insulin data are provided to permit more accurate control over a patient's glucose levels.

27 Claims, 5 Drawing Sheets

(56) References Cited

U.S. PATENT DOCUMENTS

| | | |
|---|---|---|
| 3,510,747 A | 5/1970 | Petrides |
| 3,606,592 A | 9/1971 | Madurski et al. |
| 3,750,687 A | 8/1973 | Williams |
| 3,843,455 A | 10/1974 | Bier |
| 3,923,060 A | 12/1975 | Elinwood |
| 3,930,493 A | 1/1976 | Williamson |
| 3,994,799 A | 11/1976 | Yao et al. |
| 4,018,547 A | 4/1977 | Rogen |
| 4,048,551 A | 9/1977 | Bosik |
| 4,121,282 A | 10/1978 | Ohsawa |
| 4,146,029 A | 3/1979 | Elinwood |
| 4,193,397 A | 3/1980 | Tucker et al. |
| 4,268,173 A | 5/1981 | Barnard et al. |
| 4,288,793 A | 9/1981 | Lotscher |
| 4,362,052 A | 12/1982 | Heath et al. |
| 4,401,122 A | 8/1983 | Clark, Jr. |
| 4,439,197 A | 3/1984 | Honda et al. |
| 4,441,968 A | 4/1984 | Emmer et al. |
| 4,447,224 A | 5/1984 | DeCant, Jr. et al. |
| 4,458,686 A | 7/1984 | Clark, Jr. |
| 4,464,170 A | 8/1984 | Clemens et al. |
| 4,467,811 A | 8/1984 | Clark, Jr. |
| 4,472,113 A | 9/1984 | Rogen |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,633,878 A | 1/1987 | Bombardieri |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,847,785 A | 7/1989 | Stephens |
| 4,850,959 A | 7/1989 | Findl |
| 4,851,827 A | 7/1989 | Nicholas |
| 4,866,396 A | 9/1989 | Tamura |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,688 A | 9/1991 | Murase et al. |
| 5,051,880 A | 9/1991 | Harm et al. |
| 5,061,914 A | 10/1991 | Bush et al. |
| 5,068,536 A | 11/1991 | Rosenthal |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,135,004 A | 8/1992 | Adams et al. |
| 5,139,023 A | 8/1992 | Stanley et al. |
| 5,155,695 A | 10/1992 | Stein |
| 5,190,041 A | 3/1993 | Palti |
| 5,202,261 A | 4/1993 | Musho et al. |
| 5,205,819 A | 4/1993 | Ross et al. |
| 5,207,666 A | 5/1993 | Idriss et al. |
| 5,210,778 A | 5/1993 | Massart |
| 5,211,371 A | 5/1993 | Coffee |
| 5,211,626 A | 5/1993 | Frank et al. |
| 5,223,822 A | 6/1993 | Stommes et al. |
| 5,228,449 A | 7/1993 | Christ et al. |
| 5,231,988 A | 8/1993 | Wernicke et al. |
| 5,251,126 A | 10/1993 | Kahn et al. |
| 5,262,305 A | 11/1993 | Heller et al. |
| 5,267,026 A | 11/1993 | Kawahara et al. |
| 5,278,997 A | 1/1994 | Martin |
| 5,284,423 A | 2/1994 | Holdsworth et al. |
| 5,291,614 A | 3/1994 | Baker et al. |
| 5,291,887 A | 3/1994 | Stanley et al. |
| 5,324,599 A | 6/1994 | Oyama et al. |
| 5,325,280 A | 6/1994 | Tortola et al. |
| 5,330,634 A | 7/1994 | Wong et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,384,547 A | 1/1995 | Lynk et al. |
| 5,390,671 A | 2/1995 | Lord et al. |
| 5,391,250 A | 2/1995 | Cheney, II et al. |
| 5,398,681 A | 3/1995 | Kupershmidt |
| 5,404,585 A | 4/1995 | Vimpari et al. |
| 5,406,301 A | 4/1995 | Ravid |
| 5,410,326 A | 4/1995 | Goldstein |
| 5,429,602 A | 7/1995 | Hauser |
| 5,445,611 A | 8/1995 | Eppstein et al. |
| 5,448,992 A | 9/1995 | Kupershmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,505,828 A | 4/1996 | Wong et al. |
| 5,507,288 A | 4/1996 | Bocker et al. |
| 5,517,434 A | 5/1996 | Hanson et al. |
| 5,526,844 A | 6/1996 | Kamen et al. |
| 5,533,389 A | 7/1996 | Kamen et al. |
| 5,543,678 A | 8/1996 | Hoiberg |
| 5,552,997 A | 9/1996 | Massart |
| 5,559,528 A | 9/1996 | Ravid |
| 5,568,400 A | 10/1996 | Stark et al. |
| 5,568,806 A | 10/1996 | Cheney, II et al. |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,601,435 A | 2/1997 | Quy |
| 5,604,404 A | 2/1997 | Sahara |
| 5,609,575 A | 3/1997 | Larson et al. |
| 5,615,671 A | 4/1997 | Schoonen et al. |
| 5,622,413 A | 4/1997 | Kim et al. |
| 5,622,482 A | 4/1997 | Lee |
| 5,628,324 A | 5/1997 | Sarbach |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,671,301 A | 9/1997 | Kupershmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,726,646 A | 3/1998 | Bane et al. |
| 5,741,211 A | 4/1998 | Renirie et al. |
| 5,748,103 A | 5/1998 | Flach et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,814,599 A | 9/1998 | Mitragotri et al. |

(56) References Cited

U.S. PATENT DOCUMENTS

| | | |
|---|---|---|
| 5,815,303 A | 9/1998 | Berlin |
| 5,822,715 A | 10/1998 | Worthington et al. |
| 5,825,488 A | 10/1998 | Kohl et al. |
| 5,833,603 A | 11/1998 | Kovacs et al. |
| 5,842,189 A | 11/1998 | Keeler et al. |
| 5,848,990 A | 12/1998 | Cirelli et al. |
| 5,851,197 A | 12/1998 | Marano et al. |
| 5,873,026 A | 2/1999 | Reames |
| 5,875,417 A | 2/1999 | Golden |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |
| 5,923,512 A | 7/1999 | Brownlow et al. |
| 5,947,921 A | 9/1999 | Johnson et al. |
| 5,948,512 A | 9/1999 | Kubota et al. |
| 5,951,582 A | 9/1999 | Thorne et al. |
| 5,951,836 A | 9/1999 | McAleer et al. |
| 5,954,643 A | 9/1999 | Van Antwerp et al. |
| 5,965,380 A | 10/1999 | Heller et al. |
| 5,968,011 A | 10/1999 | Larsen et al. |
| 5,971,922 A | 10/1999 | Arita et al. |
| 5,980,708 A | 11/1999 | Champagne et al. |
| 6,001,067 A | 12/1999 | Shults et al. |
| 6,002,961 A | 12/1999 | Mitragotri et al. |
| 6,011,486 A | 1/2000 | Casey |
| 6,014,577 A | 1/2000 | Henning et al. |
| 6,017,328 A | 1/2000 | Fischell et al. |
| 6,018,678 A | 1/2000 | Mitragotri et al. |
| 6,023,629 A | 2/2000 | Tamada |
| 6,024,539 A | 2/2000 | Blomquist et al. |
| 6,026,320 A | 2/2000 | Carlson et al. |
| 6,027,459 A | 2/2000 | Shain et al. |
| 6,027,496 A | 2/2000 | Loomis et al. |
| 6,027,692 A | 2/2000 | Galen et al. |
| 6,028,413 A | 2/2000 | Brockmann |
| 6,032,059 A | 2/2000 | Henning et al. |
| 6,041,253 A | 3/2000 | Kost et al. |
| 6,041,665 A | 3/2000 | Hussain |
| 6,052,565 A | 4/2000 | Ishikura et al. |
| 6,059,546 A | 5/2000 | Brenan et al. |
| 6,063,039 A | 5/2000 | Cunningham et al. |
| 6,064,368 A | 5/2000 | Kang |
| 6,066,243 A | 5/2000 | Anderson et al. |
| 6,067,017 A | 5/2000 | Stewart et al. |
| 6,067,463 A | 5/2000 | Jeng et al. |
| 6,071,249 A | 6/2000 | Cunningham et al. |
| 6,071,251 A | 6/2000 | Cunningham et al. |
| 6,073,031 A | 6/2000 | Helstab et al. |
| 6,077,660 A | 6/2000 | Wong et al. |
| 6,081,104 A | 6/2000 | Kern |
| 6,083,710 A | 7/2000 | Heller et al. |
| 6,085,871 A | 7/2000 | Karamata |
| 6,086,575 A | 7/2000 | Mejslov |
| 6,091,975 A | 7/2000 | Daddona et al. |
| 6,093,156 A | 7/2000 | Cunningham et al. |
| 6,093,172 A | 7/2000 | Funderburk et al. |
| 6,096,364 A | 8/2000 | Bok et al. |
| 6,121,009 A | 9/2000 | Heller et al. |
| 6,129,823 A | 10/2000 | Hughes et al. |
| 6,132,371 A | 10/2000 | Dempsey et al. |
| 6,141,573 A | 10/2000 | Kurnik et al. |
| 6,142,939 A | 11/2000 | Eppstein et al. |
| 6,143,164 A | 11/2000 | Heller et al. |
| 6,144,303 A | 11/2000 | Federman |
| 6,144,869 A | 11/2000 | Berner et al. |
| 6,144,922 A | 11/2000 | Douglas et al. |
| 6,147,342 A | 11/2000 | Kucher |
| 6,154,855 A | 11/2000 | Norman |
| 6,155,992 A | 12/2000 | Henning et al. |
| 6,157,442 A | 12/2000 | Raskas |
| 6,160,449 A | 12/2000 | Klomsdorf et al. |
| 6,162,202 A | 12/2000 | Sicurelli et al. |
| 6,162,611 A | 12/2000 | Heller et al. |
| 6,164,284 A | 12/2000 | Schulman et al. |
| 6,173,160 B1 | 1/2001 | Liimatainen |
| 6,175,752 B1 | 1/2001 | Say et al. |
| 6,180,416 B1 | 1/2001 | Kurnik et al. |
| 6,185,452 B1 | 2/2001 | Schulman et al. |
| 6,200,265 B1 | 3/2001 | Walsh et al. |
| 6,201,980 B1 | 3/2001 | Darrow et al. |
| 6,206,841 B1 | 3/2001 | Cunningham et al. |
| 6,208,894 B1 | 3/2001 | Schulman et al. |
| 6,212,416 B1 | 4/2001 | Ward et al. |
| 6,215,206 B1 | 4/2001 | Chitayat |
| 6,222,514 B1 | 4/2001 | DeLuca |
| 6,228,100 B1 | 5/2001 | Schraga |
| 6,232,370 B1 | 5/2001 | Kubota et al. |
| 6,233,471 B1 | 5/2001 | Berner et al. |
| 6,233,539 B1 | 5/2001 | Brown |
| 6,242,961 B1 | 6/2001 | Liu et al. |
| 6,245,060 B1 | 6/2001 | Loomis et al. |
| 6,248,067 B1 | 6/2001 | Causey, III et al. |
| 6,262,708 B1 | 7/2001 | Chu |
| 6,270,455 B1 | 8/2001 | Brown |
| 6,272,364 B1 | 8/2001 | Kurnik |
| 6,278,425 B1 | 8/2001 | DeLuca |
| 6,280,587 B1 | 8/2001 | Matsumoto |
| 6,283,926 B1 | 9/2001 | Cunningham et al. |
| 6,284,478 B1 | 9/2001 | Heller et al. |
| 6,288,653 B1 | 9/2001 | Shih |
| 6,293,925 B1 | 9/2001 | Safabash et al. |
| 6,295,506 B1 | 9/2001 | Heinonen et al. |
| 6,298,254 B2 | 10/2001 | Tamada |
| 6,298,255 B1 | 10/2001 | Cordero et al. |
| 6,299,347 B1 | 10/2001 | Pompei |
| 6,299,578 B1 | 10/2001 | Kurnik et al. |
| 6,301,499 B1 | 10/2001 | Carlson et al. |
| 6,306,104 B1 | 10/2001 | Cunningham et al. |
| 6,309,351 B1 | 10/2001 | Kurnik et al. |
| 6,309,884 B1 | 10/2001 | Cooper et al. |
| 6,312,888 B1 | 11/2001 | Wong et al. |
| 6,314,317 B1 | 11/2001 | Willis |
| 6,315,721 B2 | 11/2001 | Schulman et al. |
| 6,326,160 B1 | 12/2001 | Dunn et al. |
| 6,329,161 B1 | 12/2001 | Heller et al. |
| 6,341,232 B1 | 1/2002 | Conn et al. |
| 6,356,776 B1 | 3/2002 | Berner et al. |
| 6,359,270 B1 | 3/2002 | Bridson |
| 6,360,888 B1 | 3/2002 | McIvor et al. |
| 6,366,793 B1 | 4/2002 | Bell et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,372,371 B1 | 4/2002 | Iarochenko et al. |
| 6,375,344 B1 | 4/2002 | Hanson et al. |
| 6,375,638 B2 | 4/2002 | Nason et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,381,496 B1 | 4/2002 | Meadows et al. |
| 6,387,048 B1 | 5/2002 | Schulman et al. |
| 6,393,318 B1 | 5/2002 | Conn et al. |
| 6,403,944 B1 | 6/2002 | MacKenzie et al. |
| 6,405,066 B1 | 6/2002 | Essenpreis et al. |
| 6,408,402 B1 | 6/2002 | Norman |
| 6,417,074 B2 | 7/2002 | Kopley et al. |
| 6,419,642 B1 | 7/2002 | Marchitto et al. |
| 6,424,847 B1 | 7/2002 | Mastrototaro et al. |
| 6,425,829 B1 | 7/2002 | Julien |
| 6,427,088 B1 | 7/2002 | Bowman, IV et al. |
| 6,432,585 B1 | 8/2002 | Kawakami et al. |
| 6,437,379 B2 | 8/2002 | Kopley et al. |
| 6,438,385 B1 | 8/2002 | Heinonen et al. |
| 6,438,414 B1 | 8/2002 | Conn et al. |
| 6,440,068 B1 | 8/2002 | Brown et al. |
| 6,442,413 B1 | 8/2002 | Silver |
| 6,461,329 B1 | 10/2002 | Van Antwerp et al. |
| 6,462,162 B2 | 10/2002 | Van Antwerp et al. |
| 6,464,848 B1 | 10/2002 | Matsumoto |
| 6,466,807 B1 | 10/2002 | Dobson et al. |
| 6,466,810 B1 | 10/2002 | Ward et al. |
| 6,468,222 B1 | 10/2002 | Mault et al. |
| 6,471,689 B1 | 10/2002 | Joseph et al. |

(56) References Cited

U.S. PATENT DOCUMENTS

| | | |
|---|---|---|
| 6,471,980 B2 | 10/2002 | Sirhan et al. |
| 6,472,991 B1 | 10/2002 | Schulman et al. |
| 6,475,196 B1 | 11/2002 | Vachon |
| 6,478,736 B1 | 11/2002 | Mault |
| 6,480,730 B2 | 11/2002 | Darrow et al. |
| 6,482,158 B2 | 11/2002 | Mault |
| 6,484,045 B1 | 11/2002 | Holker et al. |
| 6,484,046 B1 | 11/2002 | Say et al. |
| 6,485,138 B1 | 11/2002 | Kubota et al. |
| 6,485,461 B1 | 11/2002 | Mason et al. |
| 6,492,180 B2 | 12/2002 | Brown et al. |
| 6,493,069 B1 | 12/2002 | Nagashimada et al. |
| 6,498,043 B1 | 12/2002 | Schulman et al. |
| 6,506,168 B1 | 1/2003 | Fathallah et al. |
| 6,513,532 B2 | 2/2003 | Mault et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,530 B2 | 2/2003 | Bang |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |
| 6,540,675 B2 | 4/2003 | Aceti et al. |
| 6,540,891 B1 | 4/2003 | Stewart et al. |
| 6,543,224 B1 | 4/2003 | Barooah |
| 6,544,212 B2 | 4/2003 | Galley et al. |
| 6,546,268 B1 | 4/2003 | Ishikawa et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,572,545 B2 | 6/2003 | Knobbe et al. |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnacaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,607,509 B2 | 8/2003 | Bobroff et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,623,501 B2 | 9/2003 | Heller et al. |
| 6,629,934 B2 | 10/2003 | Mault et al. |
| 6,633,095 B1 | 10/2003 | Swope et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,114 B1 | 12/2003 | Poulsen et al. |
| 6,656,158 B2 | 12/2003 | Mahoney et al. |
| 6,656,159 B2 | 12/2003 | Flaherty |
| 6,658,396 B1 | 12/2003 | Tang et al. |
| 6,659,948 B2 | 12/2003 | Lebel et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,675,030 B2 | 1/2004 | Ciurczak et al. |
| 6,676,816 B2 | 1/2004 | Mao et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Starkweather et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,740,518 B1 | 5/2004 | Duong et al. |
| 6,741,877 B1 | 5/2004 | Shults et al. |
| 6,743,635 B2 | 6/2004 | Neel et al. |
| 6,749,587 B2 | 6/2004 | Flaherty |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 | 8/2004 | Lilie et al. |
| 6,789,195 B1 | 9/2004 | Prihoda et al. |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,865,407 B2 | 3/2005 | Kimball et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,396 B2 | 5/2005 | Schulze et al. |
| 6,895,263 B2 | 5/2005 | Shin et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |

(56) References Cited

U.S. PATENT DOCUMENTS

| | | |
|---|---|---|
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,974,437 B2 | 12/2005 | Lebel et al. |
| 6,979,326 B2 | 12/2005 | Mann et al. |
| 6,983,176 B2 | 1/2006 | Gardner et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,015,817 B2 | 3/2006 | Copley et al. |
| 7,016,713 B2 | 3/2006 | Gardner et al. |
| 7,018,360 B2 | 3/2006 | Flaherty et al. |
| 7,020,508 B2 | 3/2006 | Stivoric et al. |
| 7,024,245 B2 | 4/2006 | Lebel et al. |
| 7,024,249 B2 | 4/2006 | Weisner et al. |
| 7,025,425 B2 | 4/2006 | Kovatchev et al. |
| 7,025,743 B2 | 4/2006 | Mann et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,046,153 B2 | 5/2006 | Oja et al. |
| 7,052,251 B2 | 5/2006 | Nason et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,092,891 B2 | 8/2006 | Maus et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,153,265 B2 | 12/2006 | Vachon |
| 7,154,398 B2 | 12/2006 | Chen et al. |
| 7,155,290 B2 | 12/2006 | Von Arx et al. |
| 7,163,511 B2 | 1/2007 | Conn et al. |
| 7,167,818 B2 | 1/2007 | Brown |
| 7,171,274 B2 | 1/2007 | Starkweather et al. |
| 7,174,199 B2 | 2/2007 | Berner et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,198,603 B2 | 4/2007 | Penner et al. |
| 7,202,734 B1 | 4/2007 | Raab |
| 7,205,409 B2 | 4/2007 | Pei et al. |
| 7,207,974 B2 | 4/2007 | Safabash et al. |
| 7,208,119 B1 | 4/2007 | Kurtock et al. |
| 7,211,048 B1 | 5/2007 | Najafi et al. |
| 7,218,017 B1 | 5/2007 | Chitayet et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,258,673 B2 | 8/2007 | Racchini et al. |
| 7,266,400 B2 | 9/2007 | Fine et al. |
| 7,276,029 B2 | 10/2007 | Goode, Jr. et al. |
| 7,278,983 B2 | 10/2007 | Ireland et al. |
| 7,283,867 B2 | 10/2007 | Strother et al. |
| 7,286,894 B1 | 10/2007 | Grant et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,317,938 B2 | 1/2008 | Lorenz et al. |
| 7,323,091 B1 | 1/2008 | Gillette et al. |
| 7,324,949 B2 | 1/2008 | Bristol et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,404,796 B2 | 7/2008 | Ginsberg |
| 7,424,318 B2 | 9/2008 | Brister et al. |
| 7,436,511 B2 | 10/2008 | Ruchti et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,775,444 B2 | 8/2010 | DeRocco et al. |
| 7,778,680 B2 | 8/2010 | Goode et al. |

(56) References Cited

U.S. PATENT DOCUMENTS

| | | |
|---|---|---|
| 7,783,333 B2 | 8/2010 | Brister et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,914,450 B2 | 3/2011 | Goode, Jr. et al. |
| 7,920,906 B2 | 4/2011 | Goode et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 8,010,174 B2 | 8/2011 | Goode et al. |
| 8,010,256 B2 | 8/2011 | Oowada |
| 8,160,900 B2 | 4/2012 | Taub et al. |
| 8,192,394 B2 | 6/2012 | Estes et al. |
| 8,216,138 B1 | 7/2012 | McGarraugh et al. |
| 8,282,549 B2 | 10/2012 | Brauker et al. |
| 8,461,985 B2 | 6/2013 | Fennell et al. |
| 8,478,557 B2 | 7/2013 | Hayter et al. |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0037060 A1 | 11/2001 | Thompson et al. |
| 2001/0037069 A1 | 11/2001 | Carlson et al. |
| 2001/0037366 A1 | 11/2001 | Webb et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0054320 A1 | 5/2002 | Ogino |
| 2002/0062069 A1 | 5/2002 | Mault |
| 2002/0068858 A1 | 6/2002 | Braig et al. |
| 2002/0068860 A1 | 6/2002 | Clark |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0095076 A1 | 7/2002 | Krausman et al. |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0147135 A1 | 10/2002 | Schnell |
| 2002/0161286 A1 | 10/2002 | Gerber et al. |
| 2002/0161288 A1 | 10/2002 | Shin et al. |
| 2002/0169394 A1 | 11/2002 | Eppstein et al. |
| 2002/0169439 A1 | 11/2002 | Flaherty et al. |
| 2002/0169635 A1 | 11/2002 | Shillingburg |
| 2002/0177764 A1 | 11/2002 | Sohrab |
| 2002/0193679 A1 | 12/2002 | Malave et al. |
| 2003/0009133 A1 | 1/2003 | Ramey |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0050575 A1 | 3/2003 | Diermann et al. |
| 2003/0060692 A1 | 3/2003 | Ruchti et al. |
| 2003/0060753 A1 | 3/2003 | Starkweather et al. |
| 2003/0060765 A1 | 3/2003 | Campbell et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnecaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0114897 A1 | 6/2003 | Von Arx et al. |
| 2003/0118460 A1 | 6/2003 | Lilie et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0147515 A1 | 8/2003 | Kai et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191377 A1 | 10/2003 | Robinson et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0199837 A1 | 10/2003 | Vachon |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208154 A1 | 11/2003 | Close et al. |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225360 A1 | 12/2003 | Eppstein et al. |
| 2003/0225361 A1 | 12/2003 | Sabra |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0018486 A1 | 1/2004 | Dunn et al. |

(56) References Cited

U.S. PATENT DOCUMENTS

| | | |
|---|---|---|
| 2004/0019321 A1 | 1/2004 | Sage et al. |
| 2004/0024553 A1 | 2/2004 | Monfre et al. |
| 2004/0027253 A1 | 2/2004 | Marsh et al. |
| 2004/0034289 A1 | 2/2004 | Teller et al. |
| 2004/0039256 A1 | 2/2004 | Kawatahara et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0063435 A1 | 4/2004 | Sakamoto et al. |
| 2004/0064088 A1 | 4/2004 | Gorman et al. |
| 2004/0064096 A1 | 4/2004 | Flaherty et al. |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0099529 A1 | 5/2004 | Mao et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0133390 A1 | 7/2004 | Osorio et al. |
| 2004/0147872 A1 | 7/2004 | Thompson |
| 2004/0152622 A1 | 8/2004 | Keith et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199056 A1 | 10/2004 | Husemann et al. |
| 2004/0199059 A1 | 10/2004 | Brauker et al. |
| 2004/0202576 A1 | 10/2004 | Aceti et al. |
| 2004/0204868 A1 | 10/2004 | Maynard et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0264396 A1 | 12/2004 | Ginzburg et al. |
| 2005/0001024 A1 | 1/2005 | Kusaka et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049179 A1 | 3/2005 | Davidson et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0090808 A1 | 4/2005 | Malave et al. |
| 2005/0096516 A1 | 5/2005 | Soykan et al. |
| 2005/0112169 A1 | 5/2005 | Brauker et al. |
| 2005/0113657 A1 | 5/2005 | Alarcon et al. |
| 2005/0113658 A1 | 5/2005 | Jacobson et al. |
| 2005/0113886 A1 | 5/2005 | Fischell et al. |
| 2005/0116683 A1 | 6/2005 | Cheng et al. |
| 2005/0118726 A1 | 6/2005 | Scultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0137530 A1 | 6/2005 | Campbell et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171512 A1 | 8/2005 | Flaherty |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0182451 A1 | 8/2005 | Griffin et al. |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203461 A1 | 9/2005 | Flaherty et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0235732 A1 | 10/2005 | Rush |
| 2005/0236361 A1 | 10/2005 | Ufer et al. |
| 2005/0238503 A1 | 10/2005 | Rush et al. |
| 2005/0238507 A1 | 10/2005 | DiIanni et al. |
| 2005/0239154 A1 | 10/2005 | Feldman et al. |
| 2005/0239518 A1 | 10/2005 | D'Agostino et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0249506 A1 | 11/2005 | Fuse |
| 2005/0249606 A1 | 11/2005 | Rush |
| 2005/0251033 A1 | 11/2005 | Scarantino et al. |
| 2005/0251083 A1 | 11/2005 | Carr-Brendel et al. |
| 2005/0261660 A1 | 11/2005 | Choi |
| 2005/0267550 A1 | 12/2005 | Hess et al. |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001550 A1 | 1/2006 | Mann et al. |

(56) References Cited

U.S. PATENT DOCUMENTS

| | | |
|---|---|---|
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0004603 A1 | 1/2006 | Peterka et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0041229 A1 | 2/2006 | Garibotto et al. |
| 2006/0052679 A1 | 3/2006 | Kotulla et al. |
| 2006/0058588 A1 | 3/2006 | Zdeblick |
| 2006/0058602 A1 | 3/2006 | Kwiatkowski et al. |
| 2006/0058627 A1 | 3/2006 | Flaherty et al. |
| 2006/0063218 A1 | 3/2006 | Bartkowiak et al. |
| 2006/0074564 A1 | 4/2006 | Bartkowiak et al. |
| 2006/0079740 A1 | 4/2006 | Silver et al. |
| 2006/0091006 A1 | 5/2006 | Wang et al. |
| 2006/0094986 A1 | 5/2006 | Neel et al. |
| 2006/0142651 A1 | 6/2006 | Brister et al. |
| 2006/0154642 A1 | 7/2006 | Scannell |
| 2006/0156796 A1 | 7/2006 | Burke et al. |
| 2006/0161078 A1 | 7/2006 | Schraga |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224141 A1 | 10/2006 | Rush et al. |
| 2006/0240403 A1 | 10/2006 | List et al. |
| 2006/0247508 A1 | 11/2006 | Fennell |
| 2006/0247985 A1 | 11/2006 | Liamos et al. |
| 2006/0253085 A1 | 11/2006 | Geismar et al. |
| 2006/0253296 A1 | 11/2006 | Liisberg et al. |
| 2006/0258929 A1 | 11/2006 | Goode et al. |
| 2006/0273759 A1 | 12/2006 | Reggiardo |
| 2006/0281985 A1 | 12/2006 | Ward et al. |
| 2006/0282290 A1 | 12/2006 | Flaherty et al. |
| 2006/0290496 A1 | 12/2006 | Peeters et al. |
| 2006/0293577 A1 | 12/2006 | Morrison et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0032706 A1 | 2/2007 | Kamath et al. |
| 2007/0032717 A1 | 2/2007 | Brister et al. |
| 2007/0038044 A1 | 2/2007 | Dobbles et al. |
| 2007/0060803 A1 | 3/2007 | Liljeryd et al. |
| 2007/0060869 A1 | 3/2007 | Tolle et al. |
| 2007/0060979 A1 | 3/2007 | Strother et al. |
| 2007/0066956 A1 | 3/2007 | Finkel |
| 2007/0078314 A1 | 4/2007 | Grounsell et al. |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan |
| 2007/0118405 A1 | 5/2007 | Campbell et al. |
| 2007/0135697 A1 | 6/2007 | Reggiardo |
| 2007/0153705 A1 | 7/2007 | Rosar et al. |
| 2007/0156094 A1 | 7/2007 | Safabash et al. |
| 2007/0163880 A1 | 7/2007 | Woo et al. |
| 2007/0173711 A1 | 7/2007 | Shah et al. |
| 2007/0173761 A1 | 7/2007 | Kanderian, Jr. et al. |
| 2007/0176867 A1 | 8/2007 | Reggiardo et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0219480 A1 | 9/2007 | Kamen et al. |
| 2007/0219597 A1 | 9/2007 | Kamen et al. |
| 2007/0228071 A1 | 10/2007 | Kamen et al. |
| 2007/0235331 A1 | 10/2007 | Simpson et al. |
| 2007/0255321 A1 | 11/2007 | Gerber et al. |
| 2007/0255348 A1 | 11/2007 | Holtzclaw |
| 2007/0271285 A1 | 11/2007 | Eichorn et al. |
| 2007/0282299 A1 | 12/2007 | Hellwig |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0021436 A1 | 1/2008 | Wolpert et al. |
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0057484 A1 | 3/2008 | Miyata et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064941 A1 | 3/2008 | Funderburk et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0103447 A1 | 5/2008 | Reggiardo et al. |
| 2008/0108942 A1 | 5/2008 | Brister et al. |
| 2008/0114228 A1 | 5/2008 | McCluskey et al. |
| 2008/0119708 A1 | 5/2008 | Budiman |
| 2008/0139910 A1 | 6/2008 | Mastrototaro et al. |
| 2008/0161666 A1 | 7/2008 | Feldman et al. |
| 2008/0177149 A1 | 7/2008 | Weinert et al. |
| 2008/0182537 A1 | 7/2008 | Manku et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200838 A1 | 8/2008 | Goldberger et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0214900 A1 | 9/2008 | Fennell et al. |
| 2008/0214915 A1 | 9/2008 | Brister et al. |

(56) References Cited

U.S. PATENT DOCUMENTS

| | | |
|---|---|---|
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1* | 9/2008 | Ray et al. .................. 702/19 |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0063402 A1 | 3/2009 | Hayter |
| 2009/0068954 A1 | 3/2009 | Reggiardo et al. |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0083003 A1 | 3/2009 | Reggiardo et al. |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0287073 A1 | 11/2009 | Boock et al. |
| 2009/0287074 A1 | 11/2009 | Shults et al. |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |

(56) References Cited

U.S. PATENT DOCUMENTS

| | | | |
|---|---|---|---|
| 2010/0119693 A1 | 5/2010 | Tapsak et al. | |
| 2010/0121169 A1 | 5/2010 | Petisce et al. | |
| 2010/0141656 A1 | 6/2010 | Krieftewirth | |
| 2010/0152554 A1 | 6/2010 | Steine et al. | |
| 2010/0160759 A1 | 6/2010 | Celentano et al. | |
| 2010/0168538 A1 | 7/2010 | Keenan et al. | |
| 2010/0168546 A1 | 7/2010 | Kamath et al. | |
| 2010/0174266 A1* | 7/2010 | Estes | 604/504 |
| 2010/0185175 A1 | 7/2010 | Kamen et al. | |
| 2010/0191082 A1 | 7/2010 | Brister et al. | |
| 2010/0191085 A1 | 7/2010 | Budiman | |
| 2010/0191472 A1 | 7/2010 | Doniger et al. | |
| 2010/0198034 A1 | 8/2010 | Thomas et al. | |
| 2010/0198142 A1 | 8/2010 | Sloan et al. | |
| 2010/0198196 A1 | 8/2010 | Wei | |
| 2010/0198314 A1 | 8/2010 | Wei | |
| 2010/0204557 A1 | 8/2010 | Kiaie et al. | |
| 2010/0213080 A1 | 8/2010 | Celentano et al. | |
| 2010/0234710 A1 | 9/2010 | Budiman et al. | |
| 2010/0240975 A1 | 9/2010 | Goode et al. | |
| 2010/0274111 A1 | 10/2010 | Say et al. | |
| 2010/0274515 A1 | 10/2010 | Hoss et al. | |
| 2010/0275108 A1 | 10/2010 | Sloan et al. | |
| 2010/0312176 A1 | 12/2010 | Lauer et al. | |
| 2010/0313105 A1 | 12/2010 | Nekoomaram et al. | |
| 2011/0024043 A1 | 2/2011 | Boock et al. | |
| 2011/0024307 A1 | 2/2011 | Simpson et al. | |
| 2011/0027127 A1 | 2/2011 | Simpson et al. | |
| 2011/0027453 A1 | 2/2011 | Boock et al. | |
| 2011/0027458 A1 | 2/2011 | Boock et al. | |
| 2011/0028815 A1 | 2/2011 | Simpson et al. | |
| 2011/0028816 A1 | 2/2011 | Simpson et al. | |
| 2011/0029269 A1 | 2/2011 | Hayter et al. | |
| 2011/0031986 A1 | 2/2011 | Bhat et al. | |
| 2011/0077490 A1 | 3/2011 | Simpson et al. | |
| 2011/0148905 A1 | 6/2011 | Simmons et al. | |
| 2011/0208027 A1 | 8/2011 | Wagner et al. | |
| 2011/0257895 A1 | 10/2011 | Brauker et al. | |
| 2011/0287528 A1 | 11/2011 | Fern et al. | |
| 2011/0320130 A1 | 12/2011 | Valdes et al. | |
| 2012/0078071 A1 | 3/2012 | Bohm et al. | |
| 2012/0108934 A1 | 5/2012 | Valdes et al. | |
| 2012/0165626 A1 | 6/2012 | Irina et al. | |
| 2012/0165640 A1 | 6/2012 | Galley et al. | |
| 2012/0173200 A1 | 7/2012 | Breton et al. | |
| 2012/0190989 A1 | 7/2012 | Kaiser et al. | |
| 2013/0035575 A1 | 2/2013 | Mayou et al. | |
| 2013/0235166 A1 | 9/2013 | Jones et al. | |

FOREIGN PATENT DOCUMENTS

| | | |
|---|---|---|
| CA | 2498682 | 9/2005 |
| CA | 2555749 | 9/2005 |
| CA | 2632709 | 6/2007 |
| CA | 2615575 | 6/2008 |
| CA | 2701374 | 4/2009 |
| EP | 0455455 | 11/1991 |
| EP | 0518524 | 12/1992 |
| EP | 0878707 | 11/1998 |
| EP | 0543916 | 7/2001 |
| EP | 1130638 | 9/2001 |
| EP | 1755443 | 11/2005 |
| EP | 1783536 | 5/2007 |
| EP | 1956371 | 8/2008 |
| EP | 2260757 | 12/2010 |
| JP | 2001-177423 | 6/2001 |
| JP | 2001-056673 | 11/2001 |
| WO | WO-96/14026 | 5/1996 |
| WO | WO-99/22236 | 5/1999 |
| WO | WO-01/52727 | 7/2001 |
| WO | WO-01/71186 | 9/2001 |
| WO | WO-02/39086 | 5/2002 |
| WO | WO-02/084860 | 10/2002 |
| WO | WO-02/100263 | 12/2002 |
| WO | WO-02/100469 | 12/2002 |
| WO | WO-03/006091 | 1/2003 |
| WO | WO-2004/015539 | 2/2004 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/003919 | 1/2006 |
| WO | WO-2006/079114 | 7/2006 |
| WO | WO-2006/086701 | 8/2006 |
| WO | WO-2007/065285 | 6/2007 |
| WO | WO-2007/149319 | 12/2007 |
| WO | WO-2008/001366 | 1/2008 |
| WO | 2008151452 A1 | 12/2008 |
| WO | 2009049252 A1 | 4/2009 |
| WO | WO-2011/104616 | 9/2011 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

PCT Application No. PCT/US2010/043132, International Search Report mailed Jan. 27, 2011.

PCT Application No. PCT/US2010/043132, International Preliminary Report on Patentability and Written Opinion of the International Searching Authority mailed Feb. 2, 2012.

Diem, P., et al., "Clinical Performance of a Continuous Viscometric Affinity Sensor for Glucose", *Diabetes Technology & Therapeutics*, vol. 6, 2004, pp. 790-799.

Garg, S., et al., "Improvement in Glycemic Excursions with a Transcutaneous, Real-Time Continuous Glucose Sensor", *Diabetes Care*, vol. 29, No. 1, 2006, pp. 44-50.

Kondepati, V., et al., "Recent Progress in Analytical Instrumentation for Glycemic Control in Diabetic and Critically Ill Patients", *Analytical Bioanalytical Chemistry*, vol. 388, 2007, pp. 545-563.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Parker, R., et al., "Robust H∞ Glucose Control in Diabetes Using a Physiological Model", *AIChE Journal*, vol. 46, No. 12, 2000, pp. 2537-2549.

European Patent Application No. 10739770.5, Examination Report mailed Apr. 30, 2013.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Li, Y., et al., "In Vivo Release From a Drug Delivery MEMS Device", *Journal of Controlled Release*, vol. 100, 2004, 99. 211-219.

Panteleon, A. E., et al., "The Role of the Independent Variable to Glucose Sensor Calibration", *Diabetes Technology & Therapeutics*, vol. 5, No. 3, 2003, pp. 401-410.

* cited by examiner

REAL TIME MANAGEMENT OF DATA RELATING TO PHYSIOLOGICAL CONTROL OF GLUCOSE LEVELS

CROSS-REFERENCES TO RELATED APPLICATIONS

This application claims the benefit of U.S. Application No. 61/228,101, filed Jul. 23, 2009, which is incorporated herein by reference in its entirety.

TECHNICAL FIELD

The present invention relates generally to an integrated diabetes management system, and more particularly, to the use of exogenous data to predict alarms and to manage glucose levels.

BACKGROUND

Glucose monitoring systems for patients afflicted with diabetes may incorporate various functionalities, including a capability to project or predict alarms to warn patients and/or provide information related to expected glucose levels, for example. Various factors may affect glucose levels; however, glucose monitoring systems generally only have access to certain types of information and factors (i.e., the monitored information). Thus, the projected alarms generated by such glucose monitoring systems are based on limited data and, although quite helpful, may be less reliable than if additional relevant information and factors were taken into account in projecting the alarms.

In a continuous glucose management ("CGM") system, it is possible to predict if the glucose level is going to cross a hypoglycemic or hyperglycemic threshold in the future by using the CGM data. One way to do this is to estimate the rate-of-change of the glucose and project from the latest glucose point to some time in the future. While this projected alarm is helpful, there can be a significant number of false alarms and misdetections. These often occur when the glucose level of the patient changes direction, which often occurs. These changes are caused by physiological effects (the body's production of insulin), insulin boluses, meal intake, exercise, and other causes.

In the past, continuous glucose monitoring and continuous insulin delivery are accomplished by different pieces of hardware devices that do not share data. Each device provides real time management tools for diabetes and insulin delivery respectively. With the convergence of continuous glucose monitoring and insulin pumps, real-time management tools could be developed that will enhance the existing tools and provide new real-time management functionalities that did not exist before.

For example, the FreeStyle Navigator® system from Abbott Diabetes Care Inc, Alameda, Calif., a continuous glucose monitor, provides a projected low glucose (hypoglycemia) alarm function using the trend of the glucose profile and the rate of change of glucose to predict when the glucose reading would fall below the low threshold that can be set by the user. The user can set the alarm sensitivity to receive a warning of up to thirty minutes prior to the low glucose event. With the addition of insulin delivery data, for example, the "insulin on board" information from the insulin pump, then we would be able to enhance the reliability of the projected low glucose alarm to be provided earlier and provide a tool for the user to figure out the amount of carbohydrates to take to prevent the low blood glucose from occurring.

As used herein, the term "exogenous" data is meant to encompass measurements other than glucose measurements.

On the other hand, many therapy parameters that govern the real time bolus decision using the insulin pump can be better adjusted and refined with the availability of the continuous glucose information. For example, many smart pumps today provide a way to calculate the amount of insulin to cover a food or meal event through the use of the carbohydrate ratio (also referred to as "carb ratio" herein) and the bolus calculator. However, the precise carbohydrate ratio to use is an empirically derived number. With the continuous glucose data available, the "accuracy" of the carbohydrate ratio used for a food bolus calculation may be assessed in real time to provide adjustment guidance for refining the carbohydrate ratio for use in the subsequent food or meal event.

Hence those of skill in the art have recognized a need for increased reliability of projected glucose alarms. Those skilled in the art have also recognized the need for the instant or near-instant incorporation of exogenous data to further increase the reliability and effectiveness of projected alarms. A further need has been recognized for providing tools to more accurately control glucose levels; and further, those skilled in the art have identified a need for the use of exogenous data in fine-tuning the management of a diabetic patient's glucose control. The present invention fulfills these needs and others.

SUMMARY OF THE INVENTION

Briefly and in general terms, the invention is directed to a system and method for processing glucose level measurement data with exogenous data to result in more reliable projected alarms and to enable tuning of patient-specific insulin data.

In accordance with the invention, there is provided an integrated glucose monitoring system, comprising a memory configured to store data relating to at least two measurements of a physiological glucose level in a patient, wherein the two measurements are taken at different time points t1 and t2, a safe range of glucose for the patient; and at least one other medically relevant patient-specific data point of exogenous data, a user interface comprising a visual display, and a processor comprising computer-executable instructions to determine a rate of change between the at least two glucose level measurements and based on the determined rate of change, further determine a glucose level at a future time t3, process the glucose level determined for time t3 with the stored exogenous data to result in an integrated glucose level for time t3, and provide an alarm at the user interface if the projected integrated glucose level for time t3 is outside the safe range.

In accordance with more detailed aspects, the exogenous data is selected from the group of insulin on board, insulin sensitivity, prior carbohydrate intake, basal rate, and available insulin bolus. The processor comprises a further computer-executable instruction to determine a recommended change to one or more of the medically relevant data points, the change comprising a therapeutic response. The recommended therapeutic response comprises one or more of an insulin bolus, intake of a particular level of carbohydrates, and temporary change to a basal insulin rate. The processor comprises a further computer-executable instruction to display the recommended therapeutic response on the visual display. The user interface comprises a graphical user interface on the visual display and an input device for communicating data and instructions from a patient to the processor, and wherein the alarm comprises a visual alarm provided on the graphical user interface.

In other aspects, the integrated glucose monitoring system further comprises a communication module configured to communicate with an insulin delivery pump engaged with the patient to acquire patient-specific insulin delivery data including insulin on board, wherein the processor processes the glucose level determined for time t3 from the rate of change data as a function of the insulin delivery data received from the delivery pump to result in the integrated glucose level for time t3. Additionally, a communication module is configured to communicate an alarm to a remote location wirelessly or by wired connection. The processor also comprises a further computer-executable instruction to control the communication module to communicate measured glucose level data, and alarms to a remote location.

In accordance with a method, there is provided a method of integrated glucose monitoring, comprising storing data relating to at least two measurements of a physiological glucose level in a patient, wherein the two measurements are taken at different time points t1 and t2, storing a safe range of glucose for the patient, storing at least one other medically relevant patient-specific data point of exogenous data, determining a rate of change between the stored at least two glucose level measurements and based on the determined rate of change, further determining a glucose level at a future time t3, processing the glucose level determined for time t3 with the stored exogenous data to result in an integrated glucose level for time t3, and providing an alarm if the projected integrated glucose level for time t3 is outside the stored safe range.

In further method aspects, the invention is directed to a method for reducing false alarms in managing projected alarms related to glucose levels, comprising determining a rate of change between at least two glucose level measurements taken at different time points t1 and t2, identifying whether an expected glucose level at a future time point t3 is above or below a target glucose level, determining a recommended change to one or more medically relevant data points comprising determining a therapeutic response if a difference between the expected glucose level and the target glucose level exceeds a preset warning value, and identifying whether the recommended change to one or more of the medically relevant data points has been performed at a predetermined time point t4 before future time point t3 has been reached, wherein an alarm is provided only where the recommended change to one or more of the medically relevant data points has not been performed at the predetermined time point t4, thereby reducing false alarms. In additional aspects, the expected glucose level is a function of the rate of change between the at least two glucose level measurements and at least one or more of the medically relevant data points. The one or more medically relevant data points is selected from the group of insulin on board, insulin sensitivity, prior carbohydrate intake, basal insulin, available insulin bolus; projection time, insulin action time, carbohydrate ratio, carbohydrate uptake time.

In yet a further detailed aspect, the recommended therapeutic response comprises one or more of a particular insulin bolus, intake of a particular level of carbohydrates, and temporary change to a basal insulin level.

An integrated glucose management system for tuning patient-specific insulin data, comprises a memory configured to record and store data representing measurements of physiological glucose levels in a patient, and to store exogenous data in the form of attributes tagged to the stored glucose measurement data, a user interface comprising a visual display and an input device configured to receive and communicate user input data and instructions, and a processor comprising computer-executable instructions to record multiple series of glucose level measurement data into the memory during defined time periods, tag each of the recorded series of glucose level measurement data with exogenous attributes including a profile name, wherein the name of the profile is selected to identify the data recording as belonging to a particular category of patient conditions, access the memory to retrieve a plurality of profiles having the same profile name, compare the recorded data of the plurality of retrieved profiles to detect a persistent pattern of undesirable measured glucose levels existing in the plurality of profiles, provide an alarm at the user interface if a persistent pattern is detected in the data of the retrieved plurality of profiles, and provide a recommended change to be made to tune the patient-specific insulin data as a result of the detected persistent pattern, and display the recommended change on the user interface.

In more detailed aspects of the integrated glucose management system, the computer-executable instructions include an excess insulin manager configured to provide a plurality of alternative recommended changes to the patient-specific insulin data. The excess insulin manager is further configured to prioritize a recommended increase in carbohydrate intake lower than recommended changes to insulin delivery. The exogenous patient-specific insulin data comprises basal rate, carb ratio, and insulin sensitivity. The profiles include a skip-meal profile, a meal test profile, and a correction bolus test profile. The processor comprises a further computer-executable instruction to require that a minimum number of profiles must be outside the safe range before a recommendation will be provided. The processor comprises a further computer-executable instruction to require that all profiles retrieved for comparison must have been recorded within a selected time period. The processor comprises a further computer-executable instruction to require that a recommendation for change of basal rate, carb ratio, and insulin sensitivity cannot exceed a predetermined amount.

In further detailed aspects, the integrated glucose management system includes a communication module permitting wireless or wired communication to and from the system to a remote location for alarms, recommended changes, patient-specific insulin data, and other data. A health care provider at a remote location may override limitations on recommended changes. Patient glucose measurements and other medical data may be stored remotely for access by the patient's health care providers or other authorized personnel.

BRIEF DESCRIPTION OF THE DRAWINGS

Various features and advantages of the disclosure will become more apparent by the following detailed description of several embodiments thereof with reference to the attached drawings, of which.

DETAILED DESCRIPTION OF THE PREFERRED EMBODIMENTS

Figure 1:
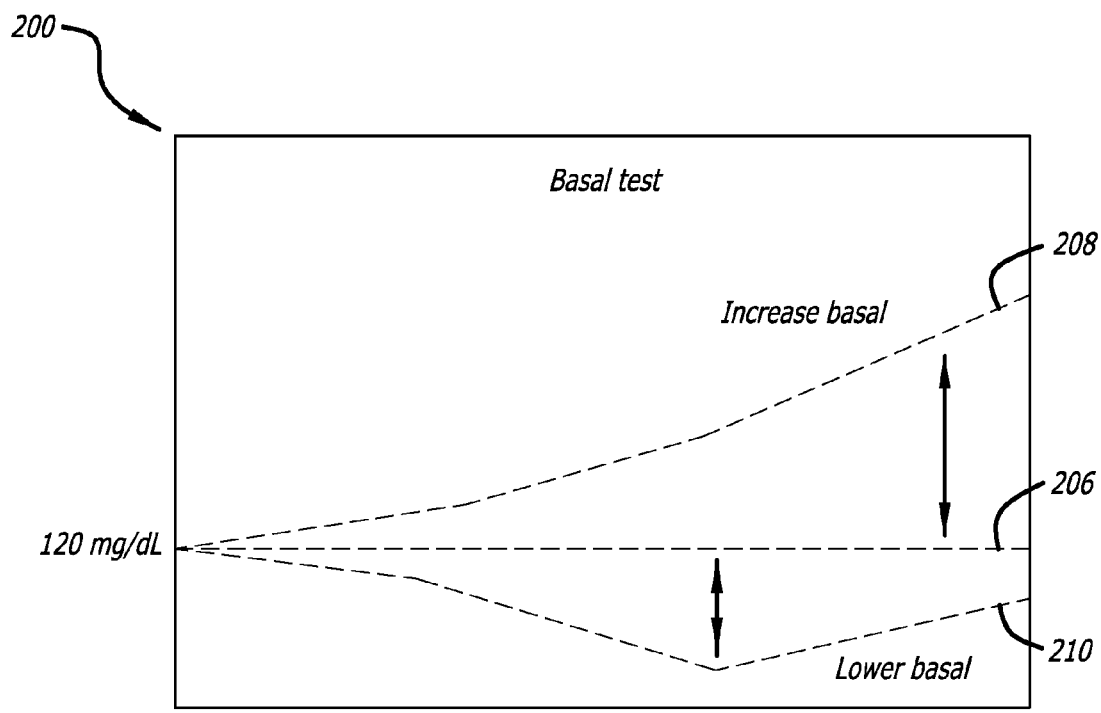
FIG. 1 is a graph providing the change in patient glucose resulting from changes in basal rate over time showing in particular the increase in glucose with a lowered basal rate and a decrease in glucose with a higher basal rate.

Reference will now be made in detail to various embodiments of the invention, examples of which are illustrated in the accompanying drawings, wherein like reference numerals refer to like or corresponding elements throughout. While the embodiments are described with detailed construction and elements to assist in a comprehensive understanding of the various applications and advantages of the embodiments, it should be apparent however that the embodiments can be carried out without those specifically detailed particulars. Also, well-known functions or constructions will not be described in detail so as to avoid obscuring the description with unnecessary detail. It should be also noted that in the drawings, the dimensions of the features are not intended to be to true scale and may be exaggerated for the sake of allowing greater understanding.

An integrated continuous glucose monitoring (CGM) and medication delivery system, such as an insulin pump, is highly advantageous as two types of information (i.e., continuous glucose monitoring information (e.g., glucose trend and profile information) and continuous insulin delivery information from the medication delivery system) may be combined for various calculations, predictions, and analyses useful in managing a person's diabetes. Examples of the calculations, predictions, and analyses include, but are not limited to: a projected alarm for providing a warning for insulin excess and carbohydrate requirements; a temporary basal manager for managing basal rate reduction through temporary basal control; a basal rate tuner for adjusting basal rate using continuous glucose information; a carbohydrate ratio tuner for adjusting carbohydrate ratio used in a bolus calculator for administering food bolus; and a correction factor tuner for adjusting insulin sensitivity in a bolus calculator for administering a correction bolus.

As used herein, the term "project" or "projected" is synonymous with "predict" or "predicted" and "forecast" or "forecasted."

As noted above, information related to meals and insulin delivery may affect a projected alarm. For example, if a projected hyperglycemia alarm were about to occur, but information related to a recent insulin bolus delivery were provided, then the projected alarm may be desirably delayed as it may be unnecessary due to the effect that the recent bolus delivery will have.

More specifically, a CGM system may predict if a glucose level is going to cross a hypoglycemic or hyperglycemic threshold based upon monitored glucose data, such as rate-of-change and the projected glucose level. However, the glucose level may change direction due to, for example, physiological effects (e.g., production of insulin), bolus, meal intake, exercise, and other factors. The change in direction may have the effect of the glucose level not crossing a threshold, thus making a projected alarm unnecessary. Thus, taking into account the factors noted above (e.g., physiological effects (e.g., production of insulin), bolus, meal intake, exercise, and other factors), it can then be determined if a projected alarm is indeed necessary, thereby increasing the efficacy of the projected alarm in its predictive capability features.

Examples of the increased reliability of the predictive capability features when insulin delivery and meal information are taken into account include the following: (i) if the projected alarm feature indicates that the hyperglycemic event was going to happen soon, but a bolus occurred ten minutes prior, the projected alarm may be cancelled; (ii) if a projected low glucose alarm was about to occur but a meal event was recently entered, the projected alarm may be cancelled; (iii) if a projected low glucose alarm was about to occur but an insulin bolus was recently given, then the projected alarm may be initiated immediately instead of waiting for the previously scheduled time; and (iv) if the presence of "exogenous" data, such as insulin on board (IOB), suggests that the patient is in an "insulin excess" state, then the projected alarm may be initiated when in the absence of the IOB information, such projected alarm would not be indicated.

To implement a projected alarm that provides a warning for insulin excess and to provide carbohydrate requirements, the following factors may by utilized to determine when a patient's glucose level will fall below an acceptable limit: current glucose level, insulin on board ("IOB"), insulin sensitivity, carbohydrate ratio, and duration of insulin action. Other factors may also be taken into account. As used herein, the "carbohydrate ratio" refers to the amount of carbohydrates required for each unit of insulin.

The two scenarios in Table 1 below may be used to illustrate the projected alarm feature, according to an embodiment, in which a patient's current glucose level is 173 mg/dL. A response in each scenario may differ depending on the availability of IOB information. The presence of IOB information can enhance the time horizon of a low glucose (hypoglycemia) projected alarm over one that is based solely on using glucose rate of change information.

TABLE 1

|  | Scenario 1 | Scenario 2 |
| --- | --- | --- |
| Current glucose | 173 mg/dL | 173 mg/dL |
| Insulin on board (IOB) | NO IOB information | 4.6 units |
| Carb ratio | 12 grams | 12 grams |
| Target glucose level | 100 mg/dL | 100 mg/dL |
| Insulin sensitivity | 45.6 mg/L | 45.6 mg/L |
| Alarm information | No alarm is indicated. | Indicate projected low glucose alarm. Glucose level will fall below low threshold of 70 mg/dL in about 2.5 hours. This calculation is based on insulin action profile, insulin action time, and insulin sensitivity. |

TABLE 1-continued

| | Scenario 1 | Scenario 2 |
|---|---|---|
| Possible Recommendation | Patient needs 1.6 units of insulin bolus. | In this example, glucose will fall below 70 mg/dL when 2.26 units of insulin are used up. Assume a linear insulin action profile for the purpose of the illustration; this is about (~49% of current insulin on board amount) 2.5 hours if time of insulin action is set at 5 hours. In addition to initiating a projected low glucose alarm, provide a potential avoidance strategy: needs 36 g of carbohydrates to cover the excess insulin. |

With scenario 2 illustrated above in Table 1, an enhanced projected hypoglycemic alarm based on the use of the exogenous insulin on board, and with the availability of personalized therapy parameters like insulin sensitivity, carb ratio, and target BG, may signal to the patient that within approximately 2.5 hours, a low glucose level will be reached.

According to another embodiment, an "excess insulin manager" can provide a recommendation to avoid the future low glucose level depending on the type of information available to the system. For example, in Table 1, Scenario 2, with the availability of the particular patient's carb ratio, the excess insulin manager can provide the recommendation to take 36 g of carbohydrates now.

A temporary basal approach, according to another embodiment, operates to determine a basal reduction necessary to compensate for excess insulin on board, when additional access and control of the insulin delivery rates are available.

With the same example in Scenario 2 of Table 1, the "excess insulin manager" can provide a different option to deal with excess insulin by reducing the future basal insulin delivery by programming a temporary basal insulin reduction. This alternative may be preferred because the user would not need to eat additional carbohydrates, which tend to add weight to the patient. Furthermore, the "excess insulin manager" could provide the means for the user to take both options to offset the excess insulin; i.e., take additional carbohydrates and make a temporary basal reduction.

Table 2 below shows that multiple recommendations may be possible after the initiation of the low alarm depending on access to insulin delivery information and control. In Table 2, Scenario 2 is the same as Scenario 2 in Table 1 except for the "possible recommendation" in that in Table 2, multiple recommendations are provided due to the presence of the basal rate information.

TABLE 2

| | Scenario 2 | Scenario 3 |
|---|---|---|
| Current glucose | 173 mg/dL | 173 mg/dL |
| Insulin on board (IOB) | 4.6 units | 4.6 units |
| Carb ratio | 12 grams | 12 grams |
| Target glucose level | 100 mg/dL | 100 mg/dL |
| Insulin sensitivity | 45.6 mg/L | 45.6 mg/dL |
| Basal insulin delivery rate | | |
| Alarm information | Indicate projected low glucose alarm. Glucose level will fall below low threshold of 70 mg/dL in about 2.5 hours. This calculation is based on insulin action profile, insulin action time, and insulin sensitivity. In this example, glucose will fall below 70 mg/dL when 2.26 units of insulin is used up. Assume a linear insulin action profile for the purpose of the illustration; this is about (~49% of current insulin on board amount) ~2.5 hours if time of insulin action is set at 5 hours. | Indicate projected low glucose alarm. Glucose level will fall below low threshold of 70 mg/dL in about 2.5 hours. This calculation is based on insulin action profile, insulin action time, and insulin sensitivity. In this example, glucose will fall below 70 mg/dL when 2.26 units of insulin is used up. Assume a linear insulin action profile for the purpose of the illustration; this is about (~49% of current insulin on board amount) ~2.5 hours if time of insulin action is set at 5 hours. |
| Recommendation | No specific insulin rate information: Needs 36 g of carbohydrates to cover the excess insulin. | With additional basal rate information: a) needs 36 g of carbohydrates to cover the excess insulin b) reduces future basal delivery to offset the excess insulin (2.34 units). Specific temp basal rate and time can be provided to facilitate quick |

TABLE 2-continued

| Scenario 2 | Scenario 3 |
|---|---|
| | setting of the rate on an integrate pump.<br>c) combination of both - wizard like process can guide the user through determining how much carbs to take and how much reduction in basal to make into the future. |

According to another embodiment, the "excess insulin manager" could be initiated by the user, instead of being initiated by the occurrence of a projected hypoglycemia alarm. The user may choose to turn off the projected alarm and use the "excess insulin manager" features on-demand. An example would be where the user wants to check for excess insulin right before going to bed so that he or she can take appropriate measures to avoid nocturnal hypoglycemia.

The production of continuous glucose data by a CGM system offers the ability to fine-tune various glucose management factors to permit more accurate control of a patient's glucose levels. For patients having an insulin pump, a basal rate of insulin delivery is typically assigned for the purpose of maintaining constant control over the patient's glucose level. Additionally, a carb ratio, mentioned above, is determined for each patient based on that patient's characteristics, which is used to determine the amount of carbohydrates that will cover, or neutralize, one unit of insulin in that particular patient. Insulin amounts and calculations of carbohydrate amounts for this patient are determined by his or her carb ratio. Also, the individual patient's sensitivity to insulin or "correction factor" is determined and is used to calculate the speed with which insulin affects the patient, also a factor in determining when and how much insulin to deliver to that patient. To provide further control over the patient's glucose, a profile recording feature is provided.

The "profile recording feature" that can be enabled by the user to record the glucose data from the CGM system as a particular "profile." User action may be used to set the start and end times of the profile recording or the user may "tag" an event in which case the processor will initiate and terminate the data recording and label that recorded data as a particular user profile. For example, the profile recording may require user input of the start time and the end time. The start time could be manually entered, or automatically entered if it corresponds to the time of certain user or device action, such as the start of a meal bolus, the start of a correction bolus, etc. The end time could be manually entered by the user or it could correspond to the completion of certain user or device action. These profiles can be categorized by the type of user actions, analyzed, and displayed in reports for use in fine-tuning glucose management factors. A specific rule engine can be implemented to provide actionable recommendations to the user based on the output of the recorded profiles.

Some examples of rules that may be implemented are: 1) rule for persistent/recurring profile, e.g., require a minimum number of profiles, N, all of which must be greater than the target or all of which must be less than the target by a certain amount X before a recommendation for a change in a factor can be given; 2) rule for usable profile for analysis; e.g., only a test measured within the last two weeks can be used for analysis for an insulin recommendation; data that is too old could be irrelevant now; 3) rule for refreshing the profile queue; more profiles must be entered into the queue after every insulin change that has taken place, or after X amount of time has elapsed since the first recording; and 4) rule for safety, that is, only allow an increase in basal insulin of ten percent at a time and set the maximum incremental change possible for the carb ratio and the correction factor.

The above rule engine settings can be set by the user or by the health care provider ("HCP") depending on the sophistication of the user. Also, the user's diabetes management devices may have possible security and lock out features so that only the HCP can set the rules without allowing the user to change them.

According to one embodiment, a "skip-meal test" feature is provided to the user to allow the user to mark the CGM data during the meal that is skipped for the purpose of fine-tuning the basal rate. Upon a user's initiating the "skip-meal test," the user will be given a chance to choose the start time of the skip-meal test (either the time when the "skip-meal test" is initiated on the user's interface ("UI"), or the user will be given the means to set a time prior to when the "skip-meal test" is initiated). The system will then record the CGM data starting from the user-indicated start time to form a skip-meal test profile. The recording of this CGM profile will end upon a certain user indication through the device UI, a spike in the CGM signal, or a certain device event (e.g., a meal bolus).

A "skip meal profile" report similar to FIG. 1 may be used to analyze and visualize the recorded "skip-meal" profiles. With reference to FIG. 1 ("Basal Rate Tuner"), a graph 200 is provided to help the user decide whether a basal rate adjustment may be needed based on the recorded "skip meal profiles." The left vertical axis provides the glucose level in mg/dL in this embodiment while the bottom horizontal axis provides time, starting with the start time of the individual profile recording. The 120 mg/dL line 206 indicates the target glucose level. The dashed line 208 above that level indicates a higher glucose level than target, which may indicate that an increase in basal rate should be affected. The dashed line 210 below target 206 indicates a low glucose and that perhaps the basal rate should be lowered. If persistent pattern is observed in the skip-meal profiles over a certain time, an appropriate action can be recommended by the "basal rate tuner" to fine-tune the basal rate to get it closer to the target level 206. However, if a persistent pattern is not observed over time, such a recommendation may not be made since the data does not clearly indicate that a continuous problem exists.

A "carb tuner" is also provided in which a "meal test" feature is provided to the user. With this feature, the meal test allows the user to start recording the CGM data to form a meal test profile after a "meal event," that profile representing the glucose response for that meal. Typically, a patient takes an insulin bolus prior to the start of a meal to manage the likely increasing spike in glucose level that eating a meal causes. That meal bolus for the patient is calculated using the patient's carb ratio. The meal test feature permits the patient to ascertain whether his or her carb ratio needs tuning.

The start of the recording of CGM data is based on a user prompt, a user entered meal event, or a device-driven event such as a meal bolus. The end of the recording of CGM data for that profile is based on user prompt or a pump device related parameter, such as the insulin action time. Appropriate meal bolus parameters such as the carb ratio will be saved as an attribute that will be associated with the profile. Additional user-entered or device related-tags, such as food description and meal type (breakfast, lunch, dinner, snack, etc.) can also be added as attributes that can be associated with the recorded profile.

Figure 2:
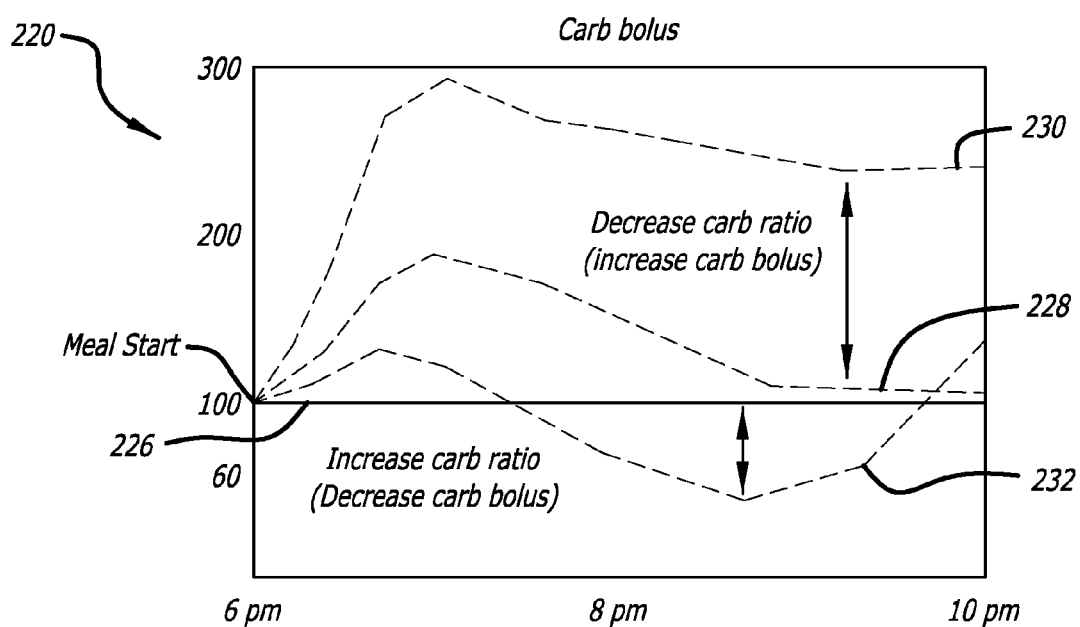
FIG. 2 is a graph that displays patient glucose versus time related to changes in carb ratio and carbohydrate bolus, according to an embodiment.

A "meal test" report, similar to that shown in FIG. 2, may be used to analyze and visualize the recorded "meal test" profiles for the purpose of fine-tuning the user's carbohydrate ratio used in a bolus calculator for recommending food bolus amounts at meal times in an integrated CGM and insulin pump system.

With further reference to FIG. 2 ("Carbohydrate Ratio Tuner"), a graph 220 provides information related to the user's carbohydrate ratio. The left vertical axis provides the user's glucose level while the bottom horizontal axis provides time. The graph illustrates when to increase the patient's carbohydrate ratio (and decrease the carbohydrate bolus) and when to decrease the patient's carbohydrate ratio (and increase the carbohydrate bolus). The 100 mg/dL solid line glucose level 226 is the target glucose level and the effects of a meal, taken at 6 pm are seen with the three representative lines. A correct carb ratio is shown with the middle dashed line 228 showing a modest increase in glucose following the mean with a drop back to near target glucose level at about 9 pm. However, the upper dashed line 230 shows an undesirable increase in glucose indicating a carb ratio that is too high. The line 230 may indicate that a decrease in the carb ratio should be determined for this patient, depending on whether a persistent pattern exists over time.

The lower dashed line 232 indicates that the glucose level dropped much lower than desired after the meal thus indicating that the carb ratio is too low and should be raised. As with the highest glucose line on the figure, i.e., line 230, a change in the carb ratio for this patient may be needed depending on whether a persistent pattern appears over a period of time. Such a persistent pattern in glucose levels, as determined by the integrated CGM and insulin pump system, is utilized to calculate a change recommendation in carb ratio for the patient. Additional data labels can be used to show the various profile attributes to interpretation.

In another embodiment, a collection of "meal test profiles" may be accessed by the patient prior to meal bolus events. A "meal bolus profile" queue may be implemented as part of the carb ratio selector during a meal bolus calculation process, in which the patient can select the carb ratio based on the previously recorded profile. The queue may indicate a carb ratio to use for meal bolus events. The results in the queue may be standardized, according to an embodiment, to group together multiple meal bolus events so that a general modification recommendation may be generated. Such collected profiles may be characterized by a particular meal, such as breakfast or other, and may be further characterized by the type of food to be eaten for that meal. The patient may then want to select the profile that provided the best glucose control for that prior event and have that previous carb ratio applied to the present meal event.

Figure 3:
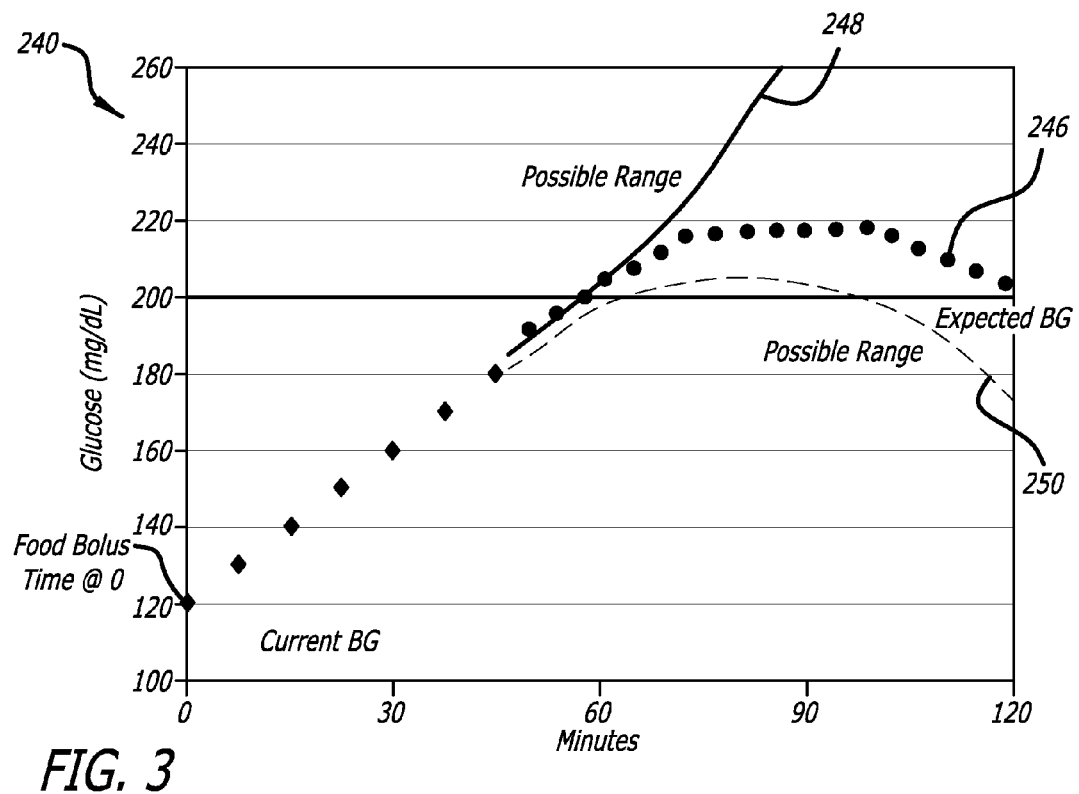
FIG. 3 is a graph that displays the effect of more accurate projected alarms when an unexpected rise in glucose occurs taking the glucose to a hyperglycemic state, showing the effect that early insulin delivery can have.

Moreover, the "meal test profile" and "carbohydrate ratio tuner" features may provide the means to add a warning mechanism for an under-bolus alarm in which under-dosing of food bolus insulin occurs if the food bolus profile deviates from an expected pattern based on the selected recorded "meal test profile". For example and with reference to FIG. 3 ("Carbohydrate Ratio Tuner—Early Warning" with glucose level at the vertical left axis and time at the bottom horizontal axis), a graph 240 is provided that indicates an expected glucose level 246, as well as possible ranges of the expected glucose level based on previously recorded profiles. A meal is consumed at 0 minutes with a glucose level of 120 mg/dL. A possible range is shown with an upper solid line 248 and the lower dashed line 250. The expected glucose level 246 is shown with the dotted line. The under-bolus alarm may be generated to indicate a need for patient intervention even if a hyperglycemia alarm is not triggered.

A third tuner is the insulin sensitivity factor or correction factor. A "correction bolus test" feature is provided to allow the user to record the CGM data profile after a correction bolus delivery for the purpose of fine-tuning the insulin sensitivity factor that may be implemented in the integrated CGM and insulin pump system. The start of the recording is based on a user prompt, a user entered correction bolus event, or a device-driven event such as a correction bolus. The end of the recording is based on a user prompt or a pump-device related parameter, such as the insulin action time. Appropriate correction bolus parameters, such as the insulin sensitivity factor, will be saved as an attribute that will be associated with the correction bolus profile. Additional user-entered or device-related tags (e.g., time of day) can also be added to the stored data as attributes that can be associated with the recorded profile.

Figure 4:
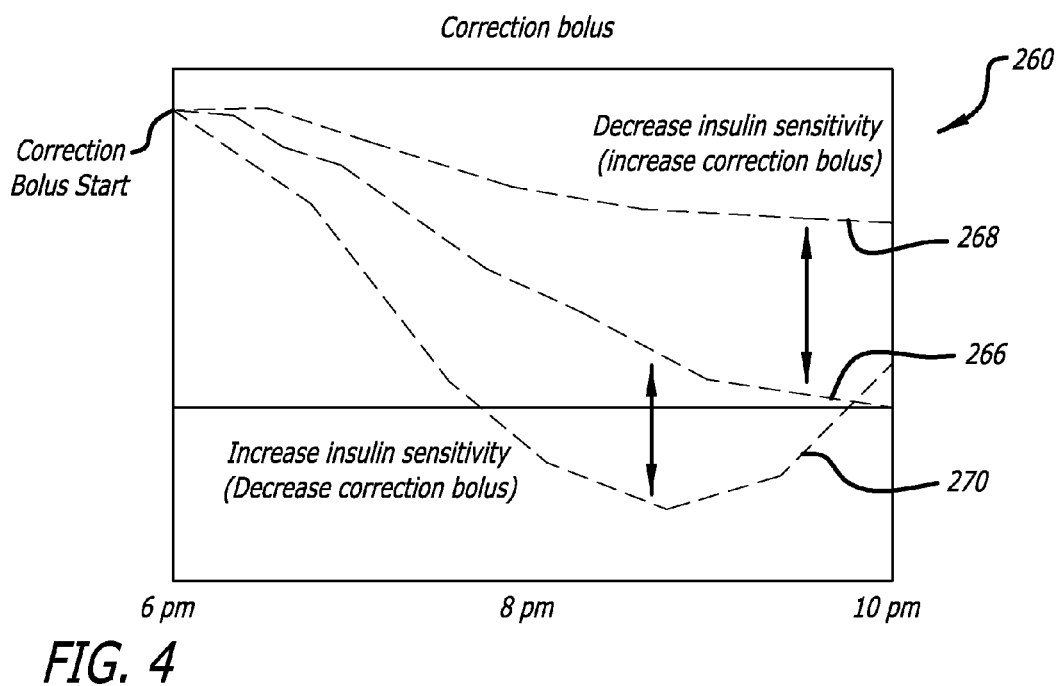
FIG. 4 is a graph of glucose versus time that illustrates the result of the delivery of a correction bolus when insulin sensitivity is considered.

A "correction bolus test' report, similar to FIG. 4, may be used to analyze and visualize the recorded "meal test" profiles for the purpose of tuning the carbohydrate ratio used in a bolus calculator for recommending food bolus amounts in an integrated CGM and insulin pump system.

With reference to FIG. 4 ("Insulin Sensitivity Tuner"), correction bolus information is displayed in graph 260, indicating a need to either increase insulin sensitivity (decrease correction bolus) or decrease insulin sensitivity (increase correction bolus). The glucose level is shown as the vertical left axis while once again time is shown as the bottom horizontal axis. In this case, all the "correction test profiles" with an insulin bolus delivery at 6 pm are plotted in a representative plot to illustrate the possible action based on the representative pattern of the profiles. The correct insulin sensitivity is shown as the middle dashed line 266. If the "correction test profiles" show a persistent pattern in regard to the upper dashed line 268 or the lower dashed line 270, appropriate actionable recommendations can be suggested to the user.

In yet another embodiment, these "correction bolus test" profiles related to insulin sensitivity adjustments may conveniently be provided prior to correction bolus events. The previously recorded profiles may be placed in a "correction bolus profile" queue for access by a patient. The results of the queue may be standardized, according to an embodiment, to group together multiple bolus results for a general modification recommendation for an upcoming correction bolus event. Should the patient experience a situation identical or similar to one of the profiles, he or she may select a profile from the queue for use of that sensitivity with the present situation.

Figure 5:
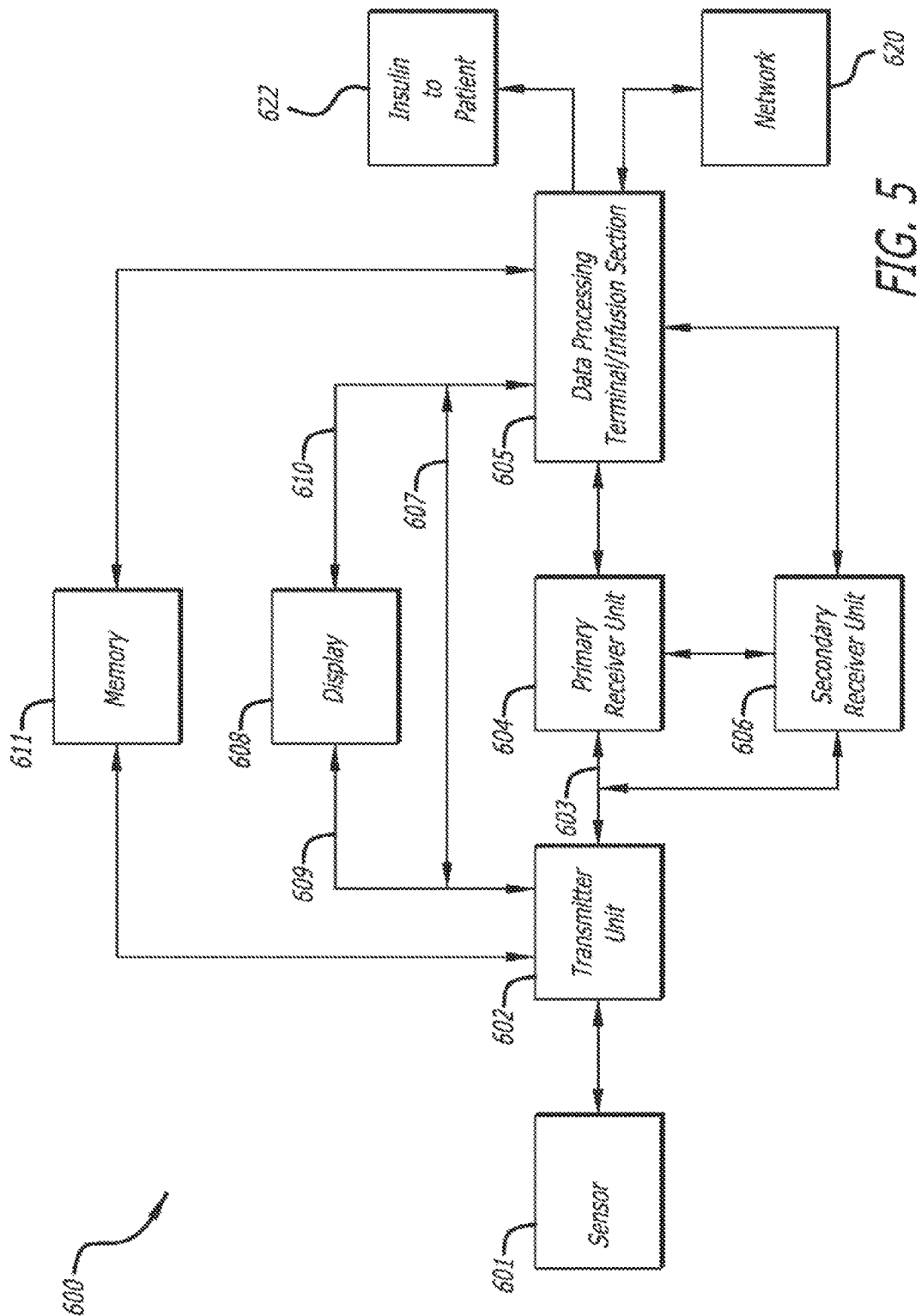
FIG. 5 illustrates a block diagram of an integrated continuous glucose monitoring and insulin pump system, according to an embodiment in which more reliable projected alarms are provided and in which profiles of continuous glucose monitoring data are produced for tuning of exogenous patient-specific insulin data for more accurate control over a patient's glucose levels.

With reference now to FIG. 5, a block diagram of an integrated CGM and insulin pump system 600, according to an embodiment, is illustrated. The integrated CGM and insulin pump system 600 may operate to manage alarm projections and alarms related to glucose levels. The system is also configured and programmed to produce profiles from CGM data to be used in tuning certain glucose management factors, as discussed above.

The system 600 may include, according to an embodiment, a glucose monitoring and management portion as well as an insulin infusion pump that stores or otherwise acts upon data relating to glucose measurements, carbohydrate intake values, and other data of interest in diabetes management.

The system 600 may include a glucose sensor 601, a transmitter unit 602 coupled to the sensor 601, and a primary receiver unit 604 which is configured to communicate with the transmitter unit 602 via a communication link 603. Those of ordinary skill in the art will readily recognize that the sensor represented as element 601 may include a drug delivery device, such as an insulin infusion system which includes a transmitter and, if so, that the principles of data preservation and transfer disclosed herein would apply as well to such a system. Therefore, system 600 as depicted in FIG. 5 will be understood to be representative rather than limiting of the arrangements of medical data receivers and transmitters with which the present invention may be used.

The primary receiver unit 604 may be configured to receive data from the transmitter unit 602 and may be further configured to transmit data to a data processing terminal/infusion section 605 for evaluating the data received by the primary receiver unit 604. Moreover, the data processing terminal/infusion section 605 in one embodiment may be configured to receive data directly from the transmitter unit 602 via a communication link 607 which may optionally be configured for bi-directional communication.

Also shown in FIG. 5 is a secondary receiver unit 606 which is operatively coupled to the communication link 603 and configured to receive data transmitted from the transmitter unit 602. Moreover, as shown in FIG. 5, the secondary receiver unit 606 is configured to communicate with the primary receiver unit 604 as well as the data processing terminal/infusion section 605. The secondary receiver unit 606 may be configured for bi-directional wireless communication with each of the primary receiver unit 604 and the data processing terminal/infusion section 605. As discussed in further detail below, in one embodiment, the secondary receiver unit 606 may be configured to include a limited number of functions and features as compared with the primary receiver unit 604. As such, the secondary receiver unit 606 may be configured substantially in a smaller compact housing, for example. Alternatively, the secondary receiver unit 606 may be configured with the same or substantially similar functionality as the primary receiver unit 604 and may be configured to be used in conjunction with a docking cradle unit for placement by bedside, for night time monitoring, for example, and/or a bi-directional communication device.

Only one sensor 601, transmitter unit 602, and data processing terminal/infusion section 605 are shown in the integrated CGM and insulin pump system 600 illustrated in FIG. 5. However, the system 600 may include one or more sensors 601, transmitter units 602, and data processing terminal/infusion sections 605. In a multi-component environment, each device is configured to be uniquely identified by each of the other devices in the system so that communication conflict is readily resolved between the various components within the system 600.

In an embodiment, the sensor 601 is physically positioned in or on the body of a user whose analyte (e.g., glucose) level is being monitored. The sensor 601 may be configured to continuously sample the analyte level of the user and convert the sampled analyte level into a corresponding data signal for transmission by the transmitter unit 602. In one embodiment, the transmitter unit 602 is physically coupled to the sensor 601 so that both devices are positioned on the user's body, with at least a portion of the analyte sensor 601 positioned transcutaneously under the skin layer of the user. The transmitter unit 602 performs data processing such as filtering and encoding on data signals, each of which corresponds to a sampled analyte level of the user, for transmission to the primary receiver unit 604 via the communication link 603.

In an embodiment, the system 600 is configured as a one-way RF communication path from the transmitter unit 602 to the primary receiver unit 604. In such embodiment, the transmitter unit 602 transmits the sampled data signals received from the sensor 601 without acknowledgement from the primary receiver unit 604 that the transmitted sampled data signals have been received. For example, the transmitter unit 602 may be configured to transmit the encoded sampled data signals at a fixed rate (e.g., at one minute intervals) after the completion of the initial power on procedure. Likewise, the primary receiver unit 604 may be configured to detect such transmitted encoded sampled data signals at predetermined time intervals. Alternatively, the integrated CGM and insulin pump system 600 may be configured with a bi-directional RF (or otherwise) communication between the transmitter unit 602 and the primary receiver unit 604.

In operation, upon completing a power-on procedure, the primary receiver unit 604 is configured to detect the presence of the transmitter unit 602 within its range based on, for example, the strength of the detected data signals received from the transmitter unit 602 or a predetermined transmitter identification information. Upon successful synchronization with the corresponding transmitter unit 602, the primary receiver unit 604 is configured to begin receiving from the transmitter unit 602 data signals corresponding to the user's analyte level as detected by the sensor 601. More specifically, the primary receiver unit 604 in an embodiment is configured to perform synchronized time hopping with the corresponding synchronized transmitter unit 602 via the communication link 603 to obtain the user's detected analyte level.

Referring again to FIG. 5, the data processing terminal/infusion section 605 may include, as examples, a personal computer, a portable computer such as a laptop or a handheld device (e.g., personal digital assistants (PDAs)), and the like, each of which may be configured for data communication with the receiver via a wired or a wireless connection. The data processing terminal/infusion section 605 includes a processor that includes computer-executable instructions for performing various functions and processing related to, for example, data transmitted and received within the system 600. Additionally, the data processing terminal/infusion section 605 may further be connected to a data network 620 for storing, retrieving, and updating data corresponding to the detected analyte level of the user, for example. Other types of data and information may also be stored, retrieved, and updated.

The data processing terminal/infusion section 605 may include an infusion device such as an insulin infusion pump or the like, which may be configured to administer insulin to a patient 622, and which may be configured to communicate with the receiver unit 604 for receiving, among others, the measured analyte level. Alternatively, the receiver unit 604 may be configured to integrate an infusion device therein so that the receiver unit 604 is configured to administer insulin therapy to patients, for example, for administering and modifying basal profiles, as well as for determining appropriate boluses for administration based on, among others, the detected analyte levels received from the sensor 601 through the transmitter unit 602.

Additionally, the transmitter unit 602, the primary receiver unit 604, and the data processing terminal/infusion section 605 may each be configured for bi-directional wireless communication such that each of the transmitter unit 602, the primary receiver unit 604, and the data processing terminal/infusion section 605 may be configured to communicate (that is, transmit data to and receive data from) with each other via the wireless communication link 603. More specifically, the data processing terminal/infusion section 605 may in an embodiment be configured to receive data directly from the transmitter unit 602 via the communication link 607, where the communication link 607, as described above, may be configured for bi-directional communication.

The data processing terminal/infusion section 605 which may include an insulin pump, may be configured to receive the analyte signals from the sensor 601 through the transmitter unit 602, and thus, incorporate the functions of the receiver unit 604 including data processing for managing the patient's insulin therapy and analyte monitoring. In an embodiment, the communication link 603 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Additional detailed description of a continuous analyte monitoring system and its various components including the functional descriptions of the transmitter are provided in U.S. Pat. No. 6,175,752 issued Jan. 16, 2001 entitled "Analyte Monitoring Device and Methods of Use," in U.S. application Ser. No. 10/745,878 filed Dec. 26, 2003, now U.S. Pat. No. 7,811,231, entitled "Continuous Glucose Monitoring System and Methods of Use," and in U.S. application Ser. No. 12/024,101 filed Jan. 31, 2008, now U.S. Pat. No. 8,140,312, entitled "Method and System for Determining Analyte Levels," each of which is assigned to the Assignee of the present application, and each of which is incorporated herein by reference.

With further reference to FIG. 5, a display 608 is provided as part of the integrated CGM and insulin pump system 600. According to an embodiment, the display 608 may be part of the data processing terminal/infusion section 605. For example, the display 608 may be a monitor of the data processing terminal/infusion section 605, which may be a personal computer or a portable computer. Alternatively, the display 608 may be a separate component coupled to the transmitter unit 602 and/or the data processing terminal/infusion section 605 respectively via communication links 609 and 610. The communication links 609 and 610, similar to the link 603 described above, may incorporate a wireless communication protocol for secure, wireless communication. Or, the communication links 609 and 610 may be directly or indirectly wired.

The display 608 may include a graphical user interface for displaying received and/or processed information to a patient or other user. The received and/or processed information may come from various and multiple sources, such as the sensor 601, the transmitter unit 602, and/or the data processing terminal/infusion section 605. For example, as described above, the transmitter unit 602 may be configured to receive data from the sensor 601, while the primary receiver unit 604 may be configured to receive data from the transmitter unit 602 and may be further configured to transmit data to the data processing terminal/infusion section 605 for evaluating the data received by the primary receiver unit 604. The evaluated data, as processed by the data processing terminal/infusion section 605, may then be displayed on the graphical user interface of the display 608, for example.

The evaluated data may be displayed in various forms and/or representations, such as charts, graphs, and/or tables. The evaluated data may simply be presented as a list or bulleted items on the display 608. According to an embodiment, the evaluated data may include graphs 200, 220, 240, and 260 as described above and as processed by the data processing terminal/infusion section 605 with both data from the sensor 601 and the insulin pump incorporated in the data processing terminal/infusion section 605.

With further reference to FIG. 5, the integrated CGM and insulin pump system 600 includes one or more memory components 611 configured to store various data and/or datasets. The one or more memory components 611 may be part of the data processing terminal/infusion section 605, and/or the one or more memory components 611 may be separate components residing, for example, in an external server or data network 620.

According to an embodiment, the memory component 611 stores data related at least to the following: measurements of a physiological glucose level in a patient (endogenous data); a target glucose level for the patient (exogenous data); and one or more medically relevant data points (exogenous data), such as insulin on board, insulin sensitivity, prior carbohydrate intake, basal rate of insulin, carb ratio, available insulin bolus, profiles of CGM data, and other. The exogenous data of a patient's basal rate, carb ratio, and insulin sensitivity are patient-specific and are related to insulin. These may also be referred to as exogenous patient-specific insulin values.

The measurements of a physiological glucose level in a patient may include two measurements taken at different time points t1 and t2, for example. The measurements may be taken from the sensor 601 at predetermined time points t1 and t2 as established by the patient or another, such as a clinician, or other health care provider. The time points t1 and t2 may be provided to the system 600 through use of the graphical user interface on the display 608. Alternatively, the time points t1 and t2 may be randomly selected by the data processing terminal/infusion section 605 based upon monitored and/or processed criteria, for example. As an example, the physiological glucose level of the patient may be continuously monitored and processed, and the data processing terminal/infusion section 605 may select two or more of the monitored levels.

The target glucose level for the patient, also stored in the memory component 611, may be established by the patient or a clinician or other healthcare professional. The target glucose level may be provided to the system 600 through use of the graphical user interface on the display 608. Alternatively, the target glucose level may be sent to the system 600 from a remote server or data network 620.

The other medically relevant data points stored in the memory component 611 may be data that is monitored and/or otherwise processed by the integrated glucose monitoring and insulin pump system 600. For example, and as described in further detail above with respect to FIGS. 1-5, the data may be exogenous and related to insulin delivery and meal information and may include, but is not limited to, insulin on board, insulin sensitivity, prior carbohydrate intake, carb ratio, basal insulin rate, and available insulin bolus. Such exogenous data, along with the target glucose level may be input to the memory 611, processor 605 and other parts of the system through various means, one of which includes a keyboard that is connected with the memory 611 or the processor 605. Such data may also be received from a remote source through the network 620 which may be in wired or wireless contact with other sources.

The computer-executable instructions of the data processing terminal/infusion section 605 may operate to process data stored in the memory component 611. For example, the instructions may operate to determine a rate of change between the glucose level measurements and an expected glucose level at a future time point t3. According to an embodiment, the time point t3 may be up to thirty minutes after the time point t2, for example. The computer-executable instructions may be further configured to identify whether this expected glucose level is above or below the target glucose level established for the patient. According to an embodiment, the expected glucose level may be a function of the rate of change between the two glucose level measurements as well as the medically relevant data point or points.

The computer-executable instructions may be further configured to provide an alarm if a difference between the expected glucose level and the target glucose level exceeds a preset warning value. The preset warning value may be established by the patient, a clinician, or other health care provider and may be provided to the system 600 through a graphical user interface of the display 608 or through other means as discussed above. The alarm may be in various forms, such as a sound alarm that serves to be audibly delivered to the patient, a visual alarm provided via the display 608 through the graphical user interface, a vibratory alarm, an email or other message delivered to a device of the patient, or a combination thereof.

The data processing terminal/infusion section 605, through the computer-executable instructions, may be further configured to determine and provide a recommended change to one or more of the medically relevant data point or points or factors. Such a recommended change may include, for example, a therapeutic response, such as a particular insulin bolus, intake of a particular level of carbohydrates, and/or a change or changes to exogenous data factors, such as the basal insulin level, the carb ratio, or the insulin sensitivity. The recommended therapeutic response may be displayed on the display 608 for ease in recognition by the patient.

The alarm and/or the recommended change may take the form of, for example, the graphs 200, 220, 240, and 260 (FIGS. 1, 2, 3, and 4). Additionally, the alarm and/or recommended change may be in the form of tables, such as Table 1 and Table 2 provided above. Profiles of CGM data may also be provided for review and selection by the patient, as discussed above. The patient may review the profiles, the comparisons of the profiles that show a persistent pattern and may retune one of more of the exogenous data in accordance with a processor's analysis of those profiles. For example, the patient may lower his or her basal rate to be consistent with the results of the profiles of the basal test by making the change on a keyboard through programming of the processor 605 or by use of a different user interface, such as the graphical user interface provided on the display 608. On the other hand, a patient may select a stored profile similar to the present conditions and command the processor to apply the stored profile's attributes to management of the patient's diabetes presently. Further, the processor may perform the safety checks of any exogenous data changes at this time to be sure that requested data changes are not inconsistent with the safety rules.

Figure 6:
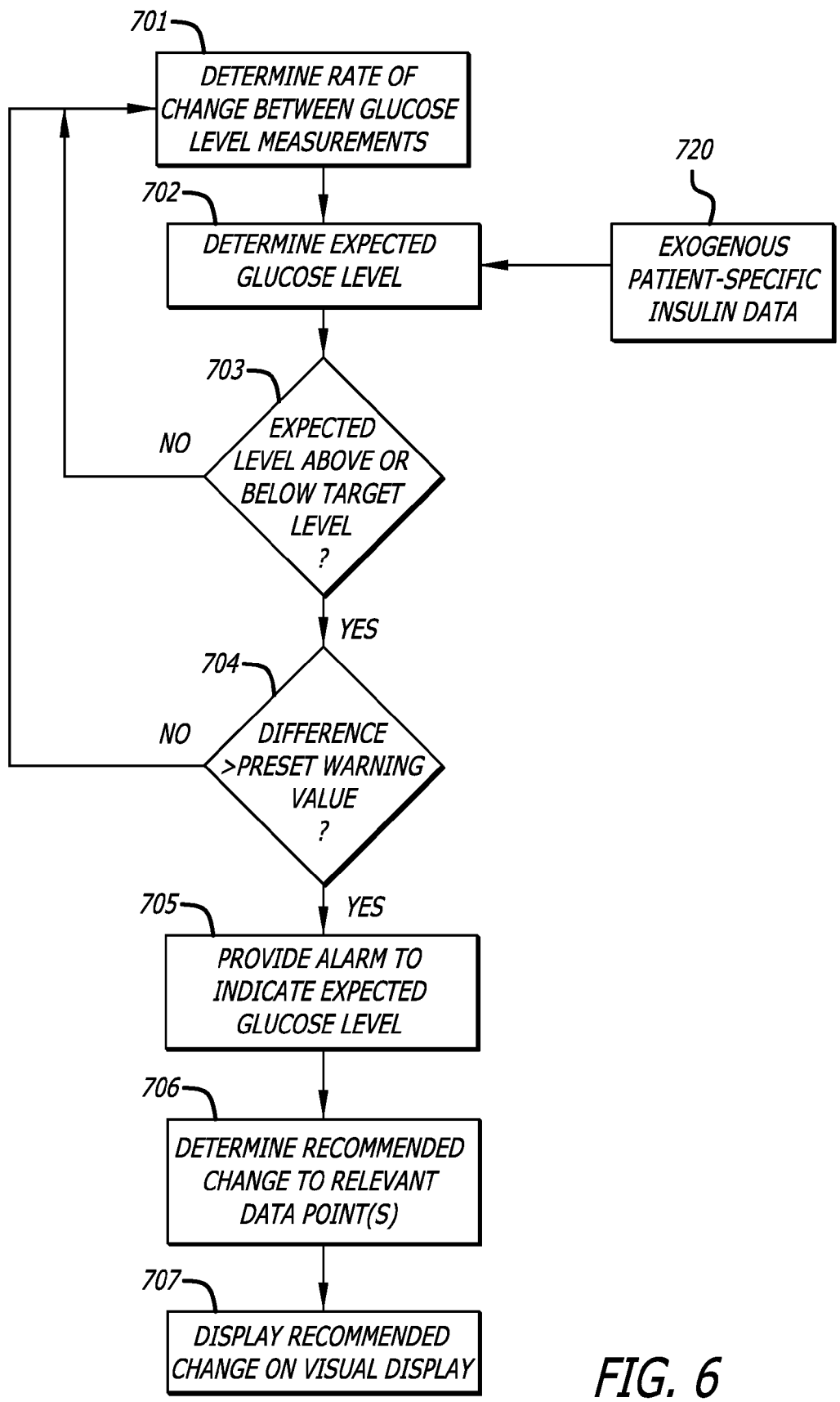
FIG. 6 is a flow chart illustrating a method for managing glucose levels, projections, and alarms related to glucose levels, according to an embodiment.

With reference to FIG. 6, a flow chart illustrates a method for managing projections and alarms related to glucose levels.

At 701, a rate of change between at least two glucose level measurements of a patient taken at different time points t1 and t2 is determined.

At 702, an expected glucose level at a future time point t3 is determined, which may be a function of the rate of change between the at least two glucose level measurements and a function of at least one other medically relevant data point selected from exogenous data, such as the group of insulin on board, insulin sensitivity, prior carbohydrate intake, basal insulin, and available insulin bolus, for example. According to an embodiment, the time point t3 may be up to thirty minutes after the time point t2. Other time intervals may be used, however, and the time point t3 may be any amount of time following the time point t1 and the time point t2.

At 703, a determination is made as to whether the expected glucose level at the time point t3, as determined at 702, is above or below a target glucose level established for the patient. If the expected glucose level is equal to the target glucose level or within a safe range, the process may continue back to 701 to determine a new rate of change between at least two glucose level measurements of the patient.

If it is determined at 703 that the expected glucose level is above or below the target glucose level or outside a safe range, a determination is made as to whether the difference between the expected glucose level and the target glucose level exceeds a preset warning value at 704, as may be established depending upon the patient and other factors. If the difference does not exceed the preset warning value, the process may continue back to 701 to determine a new rate of change between at least two glucose level measurements of the patient.

However, if the difference exceeds the preset warning value, an alarm is provided at 705 to warn the patient and/or clinician of the expected glucose level. The alarm may be one or more of a visual alarm, an audible alarm, a vibratory alarm, and a message sent to the patient and/or clinician. If the alarm is a visual alarm, the alarm may be provided on the graphical user interface of the display 608, for example.

At 706, a recommended change to one or more of the medically relevant data points is determined. The determination of the recommended change may include, for example, determining a therapeutic response, which may, include a particular insulin bolus, intake of a particular level of carbohydrates, temporary change to a basal insulin level, change carb ratio, or change insulin sensitivity. Other therapeutic or tuning responses may also be established and used.

At 707, the recommended change is displayed on a visual display, which may include a graphical user interface. For example, the recommended change may be provided on the graphical user interface.

An automatic response to an alarm may also be provided. For example, if an alarm is provided that is indicative of a very low glucose level, provision of an insulin bolus may be locked out at insulin pump system 600; e.g., by operation of a switch triggered in response to the alarm, preferably subject to manual override to ensure the availability of an insulin bolus if medically necessary.

According to embodiments of the present invention, methods are provided to increase reliability of projected alarms and reduce false alarms, which is highly desirable for improving the management of the user's medical condition. For example, in one embodiment a hyperglycemic projected alarm is provided in which false alarms are reduced. The method is provided as follows:

a) for every measurement of physiological glucose level in a patient performed by the CGM, the projected glucose is calculated based on the latest glucose reading, latest glucose trend estimate and projection time, which is generally a predetermined amount of time (e.g., 20 minutes), for example: projected glucose=current glucose+ trend*projected time;

b) if the projected glucose exceeds a predetermined hyperglycemic threshold (e.g., 300 mg/dL), then proceed to (c); and c) if an insulin bolus greater than a predetermined amount (e.g., 1 Unit) has not been delivered within a predetermined time (e.g., 20 minutes), then assert the projected alarm; otherwise, do not assert the projected alarm.

In another embodiment, a hypoglycemic projected alarm is provided in which reliability is increased and false alarms are reduced. For example, the method is provided as follows:

a) for every measurement of physiological glucose level in a patient performed by the CGM, the projected glucose is calculated based on the latest glucose reading, latest glucose trend estimate and projection time, which is generally a predetermined amount of time (e.g., 20 minutes), for example: projected glucose=current glucose+ trend*projected time;

b) if the projected glucose falls below a predetermined hypoglycemic threshold (e.g., 60 mg/dL), then proceed to (c); and c) if a meal event greater than a predetermined amount (e.g., 1 Carb) has not been delivered within a predetermined time (e.g., 20 minutes), then assert the projected alarm; otherwise do not assert the projected alarm.

In related embodiments, hyperglycemic and hypoglycemic alarms similar to those described above are contemplated in which (a) and (b) compare the current glucose level in a patient to a predetermined threshold. In other related embodiments, (c) of the above hyperglycemic and hypoglycemic alarms may be modified such that even if the event (e.g., meal or insulin bolus event) occurs within the predetermined time, if the projected glucose level exceeds a second, more extreme threshold, the alarm is asserted. One of skill in the art would understand that all predetermined parameters (e.g., predetermined amounts and times) may be selectable by the patient or user.

Varying degrees of complexity are contemplated, for the above projected hyperglycemic and hypoglycemic alarms including elaborate model-based projected alarm as described further below. Accordingly, in yet another embodiment of the present invention, a model-based projected alarm is provided in which reliability is increased and false alarms are reduced. The method is provided as follows:

a) for every measurement of physiological glucose level in a patient performed by the CGM, the projected glucose is calculated based on one or more glucose readings; projection time (predetermined, e.g., 20 minutes); an exogenous parameter or parameters, for example one or more insulin/meal/exercise information parameters (e.g., bolus or meal amount and relative time of occurrence); and/or model parameters such as insulin sensitivity, insulin action time, carbohydrate ratio, carb uptake time, basal rate, or the like; and b) if the projected glucose exceeds a predetermined hyperglycemic alarm threshold (e.g., 300 mg/dL), or falls below the hypoglycemic alarm threshold (e.g., 60 mg/dL), then the appropriate projected alarm is asserted.

In addition to potentially reducing the incidence of false alarms and thereby making projected alarms more reliable, the projected alarm may actually become more responsive with the additional inputs of meals and insulin; that is, the alarm may occur sooner than if these additional inputs were absent. For example, a patient's glucose may be at 100 mg/dL and trending downward, but not fast enough to alone trip the projected hypoglycemic alarm at this point in time. However, if a bolus occurs and is included in the projected alarm computation, the model may predict a more accurate projected glucose that will trip the projected alarm at this point in time. As discussed above, one of skill in the art would understand that all predetermined parameters described may be defined by the patient or user.

Figure 7:
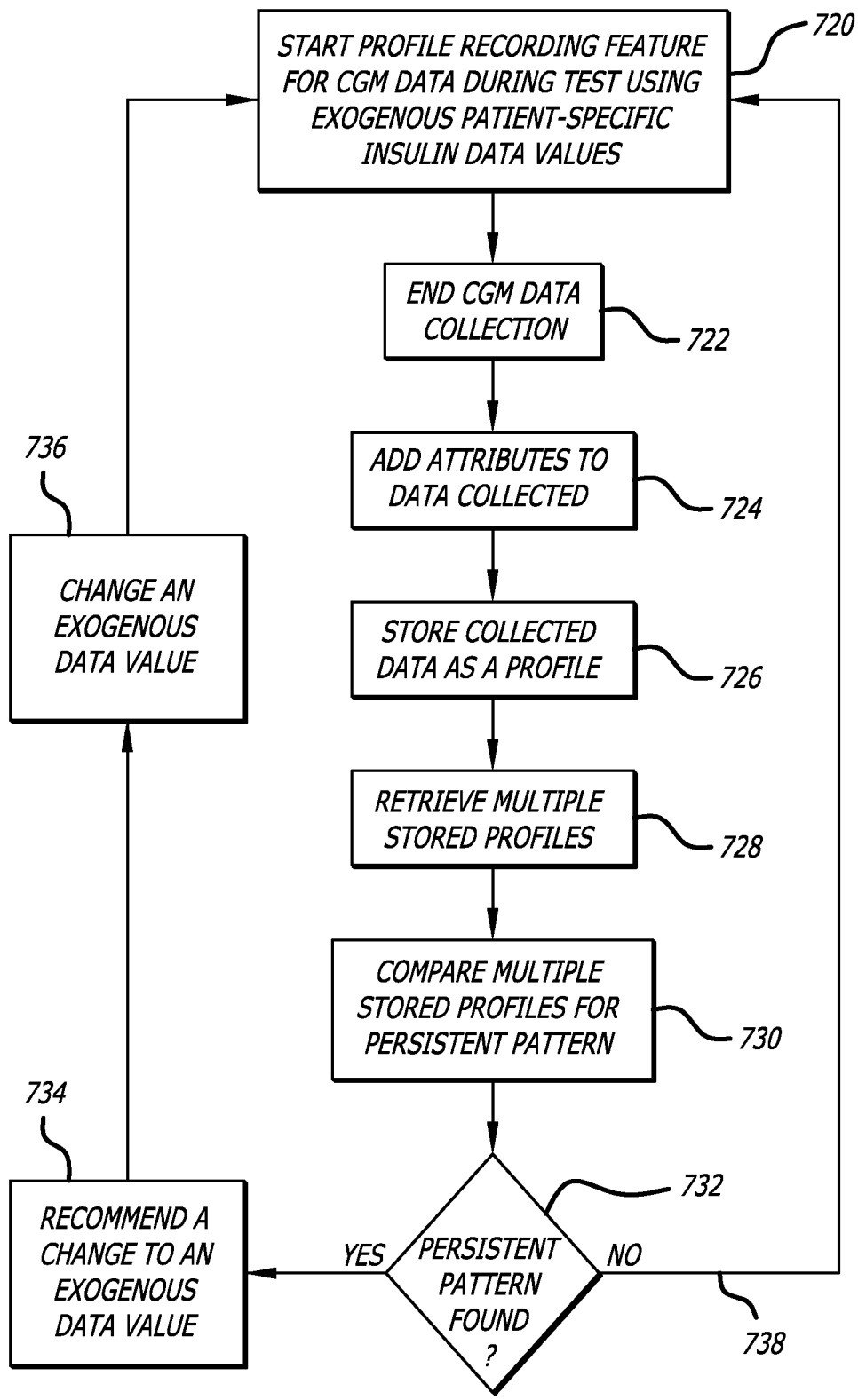
FIG. 7 is a flow chart showing a profile recording feature in accordance with aspects of the invention in which profiles are formed of continuous glucose data of the patient and are used to determine fine-tuning of patient-specific insulin values to achieve better control over a patient's glucose levels.

Turning now to FIG. 7, there is shown a flow chart of the process of forming and analyzing profiles of CGM data for "tuning" patient-specific insulin data values, such as the patient's basal delivery rate of insulin, the patient's insulin sensitivity, and the patient's carb ratio, all of which are used by the patient in the delivery of carbohydrates and insulin to control the patient's glucose levels. These tuners are discussed above.

Referring in detail to FIG. 7, the first step is one in which the recording of CGM data is started during a test or other selected time period 720, such as a basal test, skip-meal test, meal-test, or other. The means of starting the recording of the data may be a manual start signal from the patient or an automatic start control as discussed above. At the end of the test period or when sufficient CGM data has been collected, the recording feature is ended 722 either manually by the patient, such as by entering a stop signal at a keyboard, or by an automatic end recording feature, as discussed above. In certain cases, attributes are added to the recorded data file 724. As discussed above, such attributes may be varied but in one example, they may take the form of tagging the recorded CGM data as being "breakfast" data, or "high fat meal" data, or "post-prandial" data or others. Such data tagging can be highly useful in locating profiles of CGM data of similar past events that are stored in the memory 611 (FIG. 5) 726. For example when a patient intends to consume a meal similar to one recently consumed, and in which the patient's glucose was successfully controlled to the desired safe range, the patient may desire to locate the stored CGM profile for that previous meal. That stored CGM profile would include not only recorded glucose data for that meal, but would also include patient-specific insulin data values, such as the patient's basal rate, the patient's insulin sensitivity, and the patient's carb ratio. In accordance with a feature on the invention, the previously-stored similar profiles may be made available to the patient from the memory 611 on the display 608 or in printing, so that the patient may study them and select one, if desired. The patient may choose to assign those patient specific insulin values to determining the pre-meal insulin bolus for this new meal by selecting one of these stored profiles by a keyboard stroke, or by a visual touch panel stroke, or by other user interface means. Other exogenous patient data is also considered, such as insulin-on-board, in calculating the pre-meal bolus.

Stored profiles of previous events of this type are retrieved by the processor 728 from the memory 611 (FIG. 5). For example, the patient may retrieve all stored breakfast profiles. The processor then compares the stored profiles to one another to attempt to identify any persistent pattern 730. Such a pattern, as an example, may be seen in FIG. 2 in dashed line 232. Should the processor identify that in all stored profiles, or in a certain number of them, the patient's glucose level follows line 232 of FIG. 2, the processor may indicate that a persistent pattern exists in which the patient's glucose falls too low after consuming a meal. In this case, the processor would indicate in box 732 that a persistent pattern has been identified and would proceed to box 734 in which a change in the pre-meal insulin bolus is recommended so that a glucose level line more resembling 228 could be obtained. Such finding of a persistent pattern and recommended change in pre-meal insulin bolus may be presented to the patient by the display 608, it may also be stored in memory 611, it may be communicated to the patient's physician over a network 620 for storage and review by the physician or other health care provider, and/or may be printed for the patient.

The patient then has the option in this embodiment to accept the recommended exogenous data value change 736. If the change is accepted at box 736, such as a basal rate change, that change in the patient-specific insulin basal rate delivery will be implemented and the process begins again at box 720. However, if the comparison of multiple stored profiles 730 did not find a persistent pattern 738, no changes are recommended to the patient's exogenous insulin data and the process begins again at box 720.

While the disclosure has been particularly shown and described with reference to several embodiments thereof with particular details, it will be apparent to one of ordinary skill in the art that various changes may be made to these embodiments without departing from the principles and spirit of the invention, the scope of which is defined in the following claims and their equivalents.

What is claimed is:

1. An integrated glucose management system for tuning patient-specific insulin data, comprising:
    a memory configured to record and store glucose measurement data representing measurements of physiological glucose levels, and to store exogenous data in a form of attributes tagged to the stored glucose measurement data;
    a user interface comprising a visual display and an input device configured to receive and communicate user input data and instructions; and
    a processor comprising computer-executable instructions to:
        record multiple series of glucose measurement data into the memory during defined time periods;
        tag each of the recorded series of glucose measurement data with exogenous attributes including a profile name, wherein the name of the profile is selected to identify the data recording as belonging to a particular category of patient conditions;
        access the memory to retrieve a plurality of profiles having a same profile name;
        compare the retrieved plurality of profiles to detect a persistent pattern of undesirable measured glucose levels existing in the plurality of profiles;
        provide an alarm at the user interface if the persistent pattern is detected in the retrieved plurality of profiles; and
        provide a recommended change to patient-specific insulin data as a result of the detected persistent pattern, and display the recommended change on the user interface;
    wherein the computer-executable instructions include an excess insulin manager configured to provide a plurality of alternative recommended changes to the patient-specific insulin data; and further
    wherein the excess insulin manager is further configured to prioritize a recommended increase in carbohydrate intake lower than recommended changes to insulin delivery.

2. The integrated glucose management system of claim 1, wherein the patient-specific insulin data comprises a basal rate, a carb ratio, and an insulin sensitivity.

3. The integrated glucose management system of claim 1, wherein the plurality of profiles includes a skip-meal profile, a meal test profile, and a correction bolus test profile.

4. The integrated glucose management system of claim 1, wherein the processor comprises a further computer-executable instruction to require that a minimum number of the retrieved plurality of profiles must be outside a safe range before providing the recommended change to the patient-specific insulin data.

5. The integrated glucose management system of claim 1, wherein the processor comprises a further computer-executable instruction to require that the plurality of profiles retrieved for comparison must have been recorded within a selected time period.

6. The integrated glucose management system of claim 1, wherein the processor comprises a further computer-executable instruction to require that a recommendation for change of a basal rate, a carb ratio, and an insulin sensitivity cannot exceed a predetermined amount.

7. The integrated glucose management system of claim 1, wherein the processor comprises a further computer-executable instruction to record the multiple series of the glucose measurement data into the memory during the defined time periods upon receiving a manual start signal or an automatic start control.

8. The integrated glucose management system of claim 1, wherein the tag includes at least one of meal data, breakfast data, high-fat meal data, or post-prandial data.

9. The integrated glucose management system of claim 1, wherein the glucose measurement data is obtained using a glucose sensor comprising a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

10. An integrated glucose management system for tuning patient-specific insulin data, comprising:
    a memory configured to record and store glucose measurement data representing measurements of physiological glucose levels, and to store exogenous data in a form of attributes tagged to the stored glucose measurement data;
    a user interface comprising a visual display and an input device configured to receive and communicate user input data and instructions; and
    a processor comprising computer-executable instructions to:
        record multiple series of glucose measurement data into the memory during defined time periods;
        tag each of the recorded series of glucose measurement data with exogenous attributes including a profile name, wherein the name of the profile is selected to identify the data recording as belonging to a particular category of patient conditions;
        access the memory to retrieve a plurality of profiles having a same profile name;
        compare the retrieved plurality of profiles to detect a persistent pattern of undesirable measured glucose levels existing in the plurality of profiles;
        provide an alarm at the user interface if the persistent pattern is detected in the retrieved plurality of profiles;
        provide a recommended change to patient-specific insulin data as a result of the detected persistent pattern, and display the recommended change on the user interface; and
        require that a minimum number of the retrieved plurality of profiles must be outside a safe range before providing the recommended change to the patient-specific insulin data.

11. The integrated glucose management system of claim 10, wherein the patient-specific insulin data comprises a basal rate, a carb ratio, and an insulin sensitivity.

12. The integrated glucose management system of claim 10, wherein the plurality of profiles includes a skip-meal profile, a meal test profile, and a correction bolus test profile.

13. The integrated glucose management system of claim 10, wherein the processor comprises a further computer-executable instruction to require that the plurality profiles retrieved for comparison must have been recorded within a selected time period.

14. The integrated glucose management system of claim 10, wherein the processor comprises a further computer-executable instruction to record the multiple series of the glucose measurement data into the memory during the defined time periods upon receiving a manual start signal or an automatic start control.

15. The integrated glucose management system of claim 10, wherein the tag includes at least one of meal data, breakfast data, high-fat meal data, or post-prandial data.

16. The integrated glucose management system of claim 10, wherein the glucose measurement data is obtained using a glucose sensor comprising a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

17. An integrated glucose management system for tuning patient-specific insulin data, comprising:
    a memory configured to record and store glucose measurement data representing measurements of physiological glucose levels, and to store exogenous data in a form of attributes tagged to the stored glucose measurement data;
    a user interface comprising a visual display and an input device configured to receive and communicate user input data and instructions; and
    a processor comprising computer-executable instructions to:
        record multiple series of glucose measurement data into the memory during defined time periods;
        tag each of the recorded series of glucose measurement data with exogenous attributes including a profile name, wherein the name of the profile is selected to identify the data recording as belonging to a particular category of patient conditions;
        access the memory to retrieve a plurality of profiles having a same profile name;
        compare the retrieved plurality of profiles to detect a persistent pattern of undesirable measured glucose levels existing in the plurality of profiles;
        provide an alarm at the user interface if the persistent pattern is detected in the retrieved plurality of profiles;
        provide a recommended change to patient-specific insulin data as a result of the detected persistent pattern, and display the recommended change on the user interface; and
        require that a recommendation for change of a basal rate, a carb ratio, and an insulin sensitivity cannot exceed a predetermined amount.

18. The integrated glucose management system of claim 17, wherein the patient-specific insulin data comprises the basal rate, the carb ratio, and the insulin sensitivity.

19. The integrated glucose management system of claim 17, wherein the plurality of profiles includes a skip-meal profile, a meal test profile, and a correction bolus test profile.

20. The integrated glucose management system of claim 17, wherein the processor comprises a further computer-executable instruction to require that a minimum number of the retrieved plurality of profiles must be outside a safe range before providing the recommended change to the patient-specific insulin data.

21. The integrated glucose management system of claim 17, wherein the processor comprises a further computer-executable instruction to require that the plurality of profiles retrieved for comparison must have been recorded within a selected time period.

22. The integrated glucose management system of claim 17, wherein the processor comprises a further computer-executable instruction to record the multiple series of the glucose measurement data into the memory during the defined time periods upon receiving a manual start signal or an automatic start control.

23. The integrated glucose management system of claim 17, wherein the glucose measurement data is obtained using a glucose sensor comprising a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

24. A method, comprising:
    recording and storing, using a memory, glucose measurement data representing measurements of physiological glucose levels;
    storing, using the memory, exogenous data in a form of attributes tagged to the stored glucose measurement data;
    receiving and communicating, using a user interface comprising a visual display and an input device, user input data and instructions;
    recording, using a processor comprising computer-executable instructions, multiple series of glucose measurement data into the memory during defined time periods;
    tagging, using the processor comprising the computer-executable instructions, each of the recorded series of glucose measurement data with exogenous attributes including a profile name, wherein the name of the profile is selected to identify the data recording as belonging to a particular category of patient conditions;
    accessing, using the processor comprising the computer-executable instructions, the memory to retrieve a plurality of profiles having a same profile name;
    comparing, using the processor comprising the computer-executable instructions, the retrieved plurality of profiles to detect a persistent pattern of undesirable measured glucose levels existing in the plurality of profiles;
    providing, using the processor comprising the computer-executable instructions, an alarm at the user interface if the persistent pattern is detected in the retrieved plurality of profiles;
    providing, using the processor comprising the computer-executable instructions, a recommended change to patient-specific insulin data as a result of the detected persistent pattern, and display the recommended change on the user interface;
    providing, using an excess insulin manager, a plurality of alternative recommended changes to the patient-specific insulin data; and prioritizing, using the excess insulin manager, a recommended increase in carbohydrate intake lower than recommended changes to insulin delivery.

25. The method of claim 24, wherein the glucose measurement data is obtained using a glucose sensor comprising a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

26. A method, comprising:
recording and storing, using a memory, glucose measurement data representing measurements of physiological glucose levels;
storing, using the memory, exogenous data in a form of attributes tagged to the stored glucose measurement data;
receiving and communicating, using a user interface comprising a visual display and an input device, user input data and instructions;
recording, using a processor comprising computer-executable instructions, multiple series of glucose measurement data into the memory during defined time periods;
tagging, using the processor comprising the computer-executable instructions, each of the recorded series of glucose measurement data with exogenous attributes including a profile name, wherein the name of the profile is selected to identify the data recording as belonging to a particular category of patient conditions;
accessing, using the processor comprising the computer-executable instructions, the memory to retrieve a plurality of profiles having a same profile name;
comparing, using the processor comprising the computer-executable instructions, the retrieved plurality of profiles to detect a persistent pattern of undesirable measured glucose levels existing in the plurality of profiles;
providing, using the processor comprising the computer-executable instructions, an alarm at the user interface if the persistent pattern is detected in the retrieved plurality of profiles;
providing, using the processor comprising the computer-executable instructions, a recommended change to patient-specific insulin data as a result of the detected persistent pattern, and display the recommended change on the user interface; and
requiring, using the processor comprising the computer-executable instructions, that a minimum number of the retrieved plurality of profiles must be outside a safe range before providing the recommended change to the patient-specific insulin data.

27. The method of claim 26, wherein the glucose measurement data is obtained using a glucose sensor comprising a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

* * * * *